United States Patent
Alfano et al.

[11] Patent Number: 5,348,018
[45] Date of Patent: Sep. 20, 1994

[54] METHOD FOR DETERMINING IF TISSUE IS MALIGNANT AS OPPOSED TO NON-MALIGNANT USING TIME-RESOLVED FLUORESCENCE SPECTROSCOPY

[76] Inventors: Robert R. Alfano, 3777 Independence Ave., Bronx, N.Y. 10463; Asima Pradhan, 5554 Decelles, Apt. 5, Montreal, Canada; Guichen C. Tang, 2670 Valentine Ave., Apt. 9, Bronx, N.Y. 10458; Leming Wang, 142-19 Cherry Ave., Flushing, N.Y. 11355; Yury Budansky, 736 Ramapo Valley Rd., Oakland, N.J. 07436; Bidyut Baran Das, 477 W. 140 St., Apt. 62, New York, N.Y. 10031

[21] Appl. No.: 797,723

[22] Filed: Nov. 25, 1991

[51] Int. Cl.$^5$ .................................................. A61B 6/00
[52] U.S. Cl. ...................................... 128/665; 128/633; 606/3; 606/10; 606/13; 607/88; 607/89
[58] Field of Search .................... 128/665, 633, 634; 606/3, 13, 10; 607/88, 89

[56] References Cited

U.S. PATENT DOCUMENTS

| | | | |
|---|---|---|---|
| 4,556,057 | 12/1985 | Hiruma et al. | 128/634 |
| 4,682,020 | 7/1987 | Alfano | 250/214 VT |
| 4,773,097 | 9/1988 | Suzaki et al. | 128/665 |
| 4,930,516 | 6/1990 | Alfano et al. | 128/665 |
| 4,957,114 | 9/1990 | Zeng et al. | 128/665 |
| 4,981,138 | 1/1991 | Deckelbaum et al. | 128/665 |
| 5,032,714 | 7/1991 | Takahashi et al. | 250/214 VT |
| 5,039,219 | 8/1991 | James et al. | 356/318 |
| 5,042,494 | 8/1991 | Alfano | 128/395 X |
| 5,115,137 | 5/1992 | Andersson-Engels et al. | 128/634 X |
| 5,131,398 | 7/1992 | Alfano et al. | 128/665 |
| 5,137,355 | 8/1992 | Barbour et al. | 128/664 |
| 5,174,297 | 12/1992 | Daikuzono | 606/3 X |

FOREIGN PATENT DOCUMENTS

| | | | |
|---|---|---|---|
| 2002559 | 5/1990 | Canada | 128/633 |
| 222331 | 7/1983 | Japan . | |

OTHER PUBLICATIONS

Alfano et al., Journal of Quantum Electronics vol. QE23, IEEE, 1987.
Alfano et al., Journal of Quantum Electronics, vol. QE-20, No. 12, IEEE, 1984.
Lasers in Surgery and Medicine, Clarke et al., 8:45-59, 1988.
D. B. Tata et al., "Fluorescence Polarization Spectroscopy and Time-Resolved Fluorescence Kinetics of Native Cancerous and Normal Rat Kidney Tissues," Biophys. J., vol. 50, pp. 463-469 (Sep. 1986).
R. R. Alfano et al., "Steady State and Time-Resolved Laser Fluorescence from Normal and Tumor Lung and Breast Tissues," Journal of Tumor Marker Oncology, vol. 3, No. 2, pp. 165-174 (1988).

Primary Examiner—Lee S. Cohen
Assistant Examiner—Brian L. Casler
Attorney, Agent, or Firm—Kriegsman & Kriegsman

[57] ABSTRACT

A method for determining if tissue is malignant as opposed to non-malignant (i.e., benign tumor tissue, benign tissue, or normal tissue), In one embodiment, the method comprises irradiating a human breast tissue sample with light at a wavelength of about 310 nm and measuring the time-resolved fluorescence emitted therefrom at about 340 nm. The time-resolved fluorescence profile is then compared to similar profiles obtained from known malignant and non-malignant human breast tissues. By fitting the profiles to the formula $I(t) = A_1 e(-t/\tau_1) + A_2 e(-t/\tau_2)$ one can quantify the differences between tissues of various conditions. For example, non-malignant human breast tissues exhibit a slow component ($\tau_2$) which is less than 1.6 ns whereas malignant human breast tissues exhibit a slow component ($\tau_2$) which is greater than 1.6 ns. In addition, non-malignant human breast tissues exhibit a ratio of fast to slow amplitudes ($A_1/A_2$) which is greater than 0.85 whereas malignant human breast tissues exhibit a ratio of fast to slow amplitudes ($A_1/A_2$) which is less than 0.6. This technique can be used with different excitation and/or emission wavelengths, and can be applied to the detection of malignancies (or other abnormal states) in tissues other than human breast tissue.

16 Claims, 24 Drawing Sheets a1=2.59, t1=120ps, a2=4.33, t2=2.3ns a1=2, t1=83.59ps, a2=4.8, t2=2.7ns

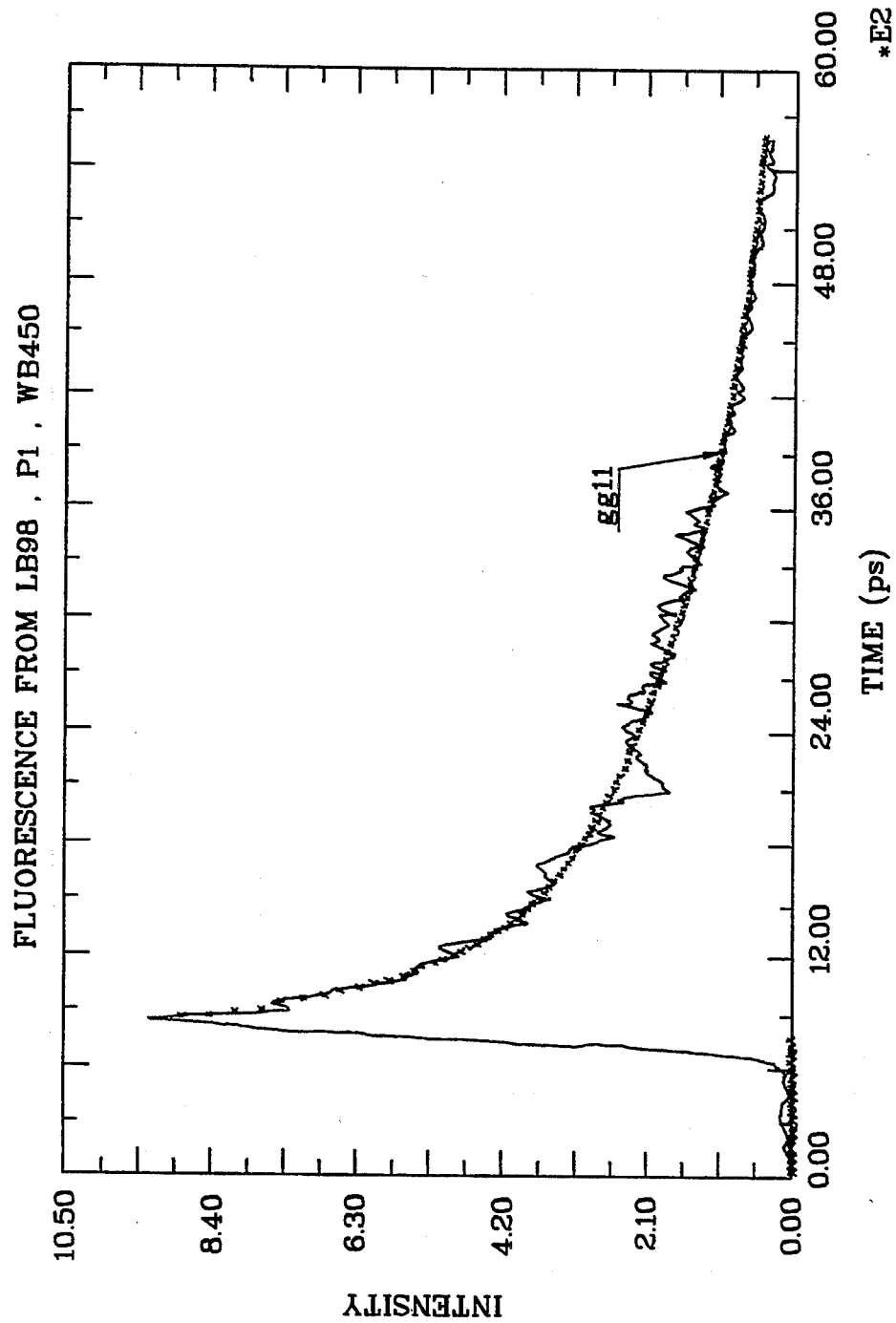

a1=56, t1=178ps, a2=107, t2=2.77ns

METHOD FOR DETERMINING IF TISSUE IS MALIGNANT AS OPPOSED TO NON-MALIGNANT USING TIME-RESOLVED FLUORESCENCE SPECTROSCOPY

BACKGROUND OF THE INVENTION

The present invention relates generally to methods for detecting malignant tissue and more particularly to a method for detecting malignant tissue using time-resolved fluorescence spectroscopy.

As can readily be appreciated, the detection of malignant cancerous) tissue is often a prerequisite to its treatment.

In U.S. Pat. No. 4,930,516, which is issued on Jun. 5, 1990 Alfano et al. as inventors, a method and an apparatus for detecting the presence of cancerous tissue using visible luminescence are described. According to the teachings of this patent, the tissue to be examined is excited with a beam of monochromatic light that causes the tissue to fluoresce over a spectrum of wavelengths. The intensity at which the excited tissue fluoresces can be measured either over a spectrum or at a predetermined number of preselected wavelengths. By determining the wavlengths at which maximum intensities are attained for the tissue in question and by comparing these peak wavelengths, either visually or electronically, to the peak wavelengths derived from a known non-cancerous tissue, or by comparing the spectrum of the excited tissue with the spectrum of a known noncancerous tissue one can determine the carcinomatoid status of the tissue in question. The invention is based on the discovery that the visible luminescence spectra for cancerous and non-cancerous tissue are substantially different and that the differences are such that visible luminescence from tissue can be used to detect the presence of cancer.

In U.S. Pat. No. 5,042,494, which issued on Aug. 27, 1991 with Alfano as inventor, a method and an apparatus for detecting the presence of cancerous tissue using native visible luminescence are described. The tissue to be examined is excited with a beam of monochromatic light that causes the tissue to fluoresce over a spectrum of wavelengths. The intensity at which the excited tissue fluoresces can be measured either over a spectrum or at a predetermined number of preselected wavelengths. By determining the wavelengths at which maximum intensities are attained for the tissue in question and by comparing these peak wavelengths, either visually or electronically, to the peak wavelengths derived from a known non-cancerous tissue, or by comparing the luminescence spectrum of the excited tissue with the luminescence spectrum of a known noncancerous tissue and/or known cancerous tissue or the excitation spectrum of the excited tissue with the excitation spectra or known cancerous and/or known non-cancerous tissues one can determine the carcinomatoid status of the tissue in question. Once it has been determined that the tissue is cancerous, it may be destroyed by ablation by exposing it to a beam of light from a high power laser. The invention is based on the discovery that the visible luminescence spectra for cancerous and non-cancerous tissues are substantially different and that the differences are such that visible luminescence from the tissue can be used to detect the presence of cancer and also on the discovery that the spectral profiles or excitation spectra are similarly different.

In Japanese Pat. No. Hei2-22331, which was laid open on Jul. 13, 1983 and which issued on May 18, 1990 with Nishizaka et el. as inventors, a method and a device for detecting abnormal tissue, such as cancerous tissue, by spectroanalysis are described. The method of the present invention comprises the steps of directing a laser beam onto various samples, analyzing the spontaneous emission caused in the samples, and analyzing the change in the physical characteristics of the samples. Various laser beams, such as the single wave or tunable laser pulse or continuous-mode oscillation laser, are applicable for the excitation of the sample cells. In addition, various spectra are used, such as the wave spectrum, time resolved spectrum, fluorescence spectrum, Raman spectrum and polarized light spectrum. The use of a single spectrum as well as a combination of two or more of the spectra is possible.

In copending and commonly assigned U.S. patent application Ser. No. 07/468,633, filed on Jan. 22, 1990 with Alfano et al. as inventors, a method and an apparatus for distinguishing cancerous tumor tissue from benign tumor tissue, benign tissue and normal tissue using native fluorescence are described. The tissue to be examined is excited with a beam of monochromatic light at about 300 nm. The intensity of the native fluorescence emitted from the tissue is measured at about 340 and 440 nm. The ratio of the two intensities is then calculated and used as a basis for determining if the tissue is cancerous as opposed to benign or normal. The invention is based on the discovery that when cancerous tissue is excited with monochromatic light at about 300 nm, the native fluorescence spectrum over the region from about 320 nm to 600 nm is substantially different from the native fluorescence spectrum that would result if the tissue were either benign or normal. The technique is useful in vivo and in vitro testing of human as well as animal tissue.

In U.S. Pat. No. 4,957,114, which issued on Sep. 18, 1990 with Zeng et al. as inventors, a diagnostic apparatus for intrinsic fluorescence of malignant tumors and a method for using the apparatus for diagnosis are described. The apparatus employs an ultraviolet light source with an emitting waveband of 3000A-4000A. Light from the light source is transmitted through a bundle of quartz optic fibers to the surface of the tumor, whether benign or malignant, to stimulate it, which then generates a specific intrinsic fluorescence spectrum. The intrinsic fluorescence spectrum reflected from the surface of the tumor is transmitted by a second bundle of glass fibers placed near it to a color resolution means, then processed by a scanning means and a circuit means, and dIsplayed and recorded by a display recording means. The display may be a graphic presentation of the intrinsic fluorescence spectrum of the tumor that is tested. If the graphic presentation displayed includes a single peak within the range of the blue color band, it indicates that the tumor being tested is bengin. If however, a second peak appears within the range of the red band of the graphic presentation it is a characteristic peak of malignancy, indicating the existence of a malignant tumor. The presence of the red color can be established by eye rather than a complex resolution system.

In copending and commonly assigned U.S. patent application Ser. No. 07/651,449 filed on Feb. 7, 1991 with Alfano et al. as inventors, a method for determining if a tissue is a malignant tumor tissue, a bengin tumor tissue, on a benign or normal tissue using Raman spectroscopy is described. The method is based on the discovery that, when irradiated with a beam of infrared, monochromatic light, malignant tumor tissue, benign tumor tissue, and normal or benign tissue produce distinguishable Raman spectra. For human breast tissue, some salient differences in the respective Raman spectra are the presence of four Raman bands at a Raman shift of about 1079, 1300, 1445 and 1659 cm$^{-1}$ for normal or benign tissue, the presence of three Raman bands at a Raman shift of about 1240, 1445 and 1659 cm$^{-1}$ for benign tumor tissue, and the presence of two Raman bands at a Raman shift of about 1445 and 1659 cm$^{-1}$ for malignant tumor tissue. In addition, it was discovered that for human breast tissue the ! ratio of intensities of the Raman bands at a Raman shift of about 1445 and 1659 cm$^{-1}$ is about 1.25 for normal or benign tissue, about 0.93 benign tumor tissue, and about 0.87 for malignant tumor tissue.

SUMMARY OF THE INVENTION

It is an object of the present invention to provide a new method for determining if tissue is malignant as opposed to non-malignant (i.e., benign tumor, benign, or normal).

It is another object of the present invention to provide a new method for determining if tumorous tissue is malignant as opposed benign.

It is yet another object of the present invention to provide a method for detecting malignant tumor tissue which does not require the use of X-ray sensitive plates, photodetectors or ultrasound.

It is still another object of the present invention to provide a method for detecting malignant tissue which can be used either in vivo or in vitro.

The present invention is based on the surprising discovery that the time-resolved fluorescence spectra obtained from malignant tissues are distinguishable, in many instances, from the time-resolved fluorescence spectra obtained from corresponding non-malignant tissues (i.e., benign tumor tissues, benign tissues, or normal tissues). This was demonstrated, in one instance, by exciting various samples of malignant human breast tissue, benign human breast tumor tissue, benign human breast tissue, and normal human breast tissue with picosecond light pulses having a wavelength of about 310 nm, measuring the time-resolved native fluorescence emitted therefrom at a wavelength of about 340 nm, and comparing the respective spectral. As a means of quantifying some of the differences in the respective spectra, the profiles were fitted to the double exponential $I(t) = A_1 e(-t/\tau_1) + A_2 e(-t/\tau_2)$ by the least square method and differences were noted In the respective slow components ($\tau_2$) and in the respective ratios of fast amplitude ($A_1$) to slow amplitude ($A_2$).

Additionally, differences in the respective spectra of malignant human breast tissue samples and benign human breast tumor tissue samples were also observed by exciting the tissue samples with picosecond light pulses at a wavelength of about 353 nm and then measuring the time-resolved native fluorescence emitted therefrom at wavelengths of about 400 nm, about 450 nm and about 500 nm. Examples of distinguishing features included differences in the respective fast components ($\tau_1$) and slow components ($\tau_2$) of the various spectra.

Furthermore, differences in the respective spectra of malignant human breast tissue samples and normal human breast tissue samples were also observed by exciting the tissue samples with picosecond light pulses at a wavelength of about 530 nm and then measuring the time-resolved native fluorescence emitted therefrom at a wavelength of about 600 nm. An example of a distinguishing feature included dffferences in the respective fast components ($\tau_1$) of the various spectra.

Differences in the time-resolved spectra for malignant and non-malignant lung and ovarian tissue samples were also observed. For example, when malignant and normal lung tissue samples were excited with picosecond light pulses at a wavelength of about 530 nm and then measured over time at a wavelength of about 600 nm, an appreciable difference was discovered in their respective fast components ($\tau_1$). Similarly, when malignant and normal ovarian tissue samples were excited with picosecond light pulses at a wavelength of about 351 and then measured at a wavelength of about 450 nm. differences were discovered in both the respective-fast components ($\tau_1$) and slow components ($\tau_1$).

As can readily be appreciated, it is expected that time-resolved fluorescence spectroscopy can also be used to detect cancer in tissues located, for example, in the cervix, the colon, the kidneys, the brain, the gastrointestinal tract, the prostate, the bladder, the liver, the pancreas, the heart, and the stomach. In addition, it is also expected that time-resolved fluorescence spectroscopy can be used to detect diseased states in various biomedical materials, such as atherosclerosis in blood vessels, leukemia in white blood cells, kidney stones In kidneys, etc.

Other objects, features, and advantages of the present Invention will be set forth In part in the description which follows, and in part will be obvious from the description or may be learned by practice of the invention. The objects, features and advantages of the present invention may be realized and attained by means of the instrumentalities and combinations particularly pointed out in the appended claims.

BRIEF DESCRIPTION OF THE DRAWINGS

The accompanying drawings, which are hereby incorporated into and constitute a part of this specification, illustrate the preferred embodiments of the invention and, together with the description, serve to explain the principles of the invention. In these drawings wherein like reference numerals represent like parts:

FIGS. 5(a) and 5(b) are time-resolved fluorescence profiles of two benign human breast tumor tissue samples, the profiles being obtained by exciting the samples with light at a wavelength of about 353 nm and then measuring for a period of time the native fluorescence emitted therefrom at a wavelength of about 450 nm:

DETAILED DESCRIPTION OF PREFERRED EMBODIMENTS

The present invention is directed to a new method for determining if tissue is malignant as opposed to non-malignant (i.e., benign tumor, benign tissue, or normal). This method Is premised on the discovery that, under certain conditions, the time-resolved fluorescence profile of a malignant tissue is distinguishable from that of a corresponding non-malignant tissue. The present inventors believe that such differences are attributable, at least in part, to microenvironmental changes which take place within malignant cells and which affect the time-resolved fluorescence properties of naturally-occurring fluorophores present within the cells. Examples of fluorophores which are believed to be affected in the manner described above include tryptophan, various nucleotides, particularly nicotinamlde adeninc dinucleotide hydride (NADH), flayins, colingan, and alastin. Such molecules are present, to some extent, in virtually every type of tissue although the amount of any given type of molecule typically varies from tissue to tissue. Generally speaking, steady-state fluorescence of tryptophan and, to a lesser extent, NADH alastin, and collagen can be achieved by excitation with light at a wavelength of about 300 nm. In addition, excitation with light at a wavelength of about 850 nm typically causes both NADH and flayins fluoresce. Moroever, excitation with light at a wavelength of about 30 nm typically causes flavins to fluoresce. Consequently, excitation with light at one or more of the above-mentioned wavelengths Is a good starting point for selection of an appropriate excitation wavelength that will permit one to detect differences in the time-resolved fluorescence of malignant and non-malignant tissues. (As will be seen below, an appropriate fluorescence wavelength must also be selected.) It should be understood that other excitation wavelengths, besides the three described above, may also be appropriate and, furthermore, that additional fluorophores may exist, which may or may not be excited at the above-mentioned wavelengths.

Figure 1:
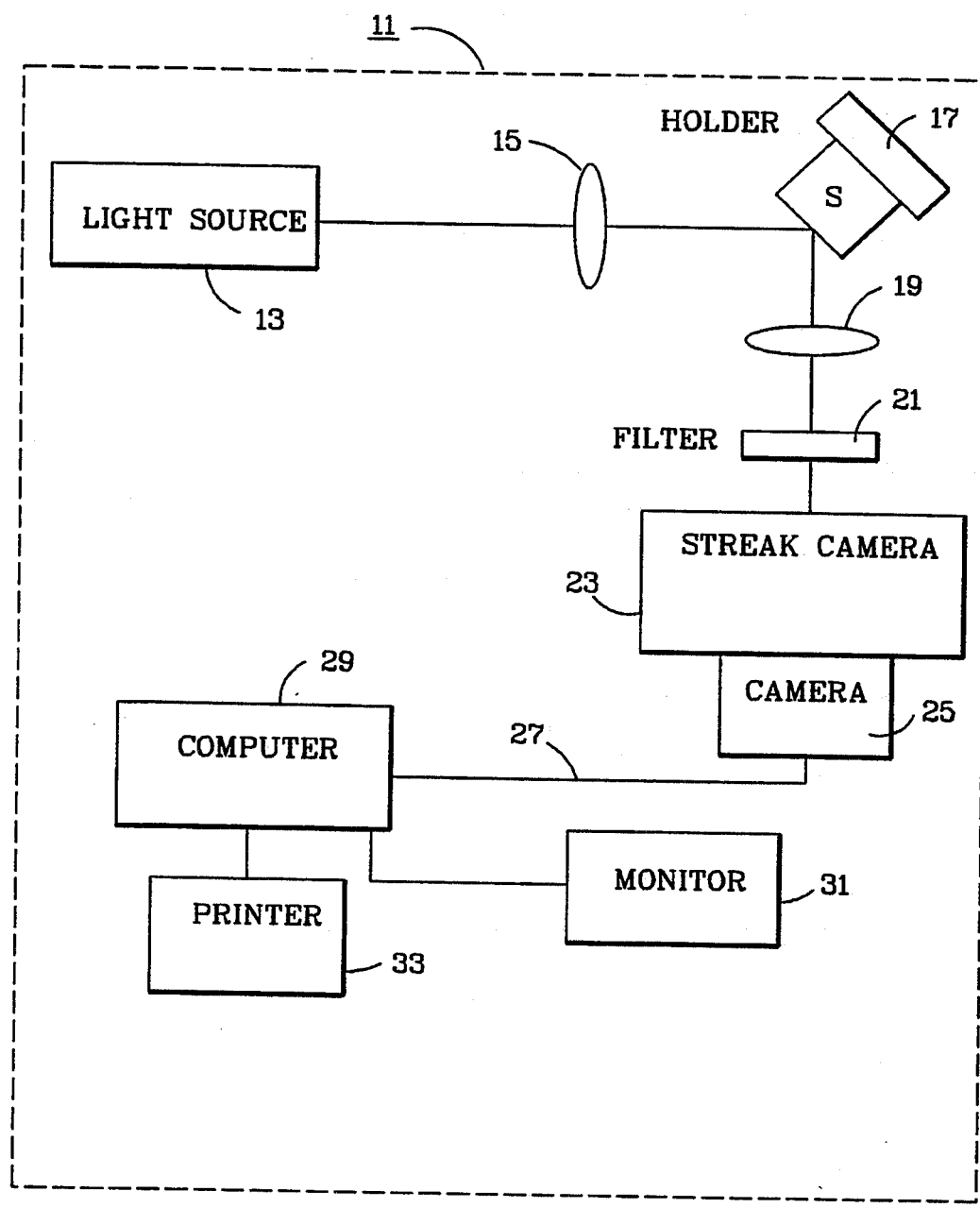
FIG. 1 is a schematic diagram of one embodiment of a time-resolved fluorescence spectroscopy system which may be used to perform the method of the present invention.

Referring now to FIG. 1, there is shown a schematic diagram of one embodiment of a time-resolved fluorescence spectroscopy system which may be used to perform the method of the present invention, the system being represented by reference numeral 11.

System 11 includes a light source 13, such as a laser, for generating light used to excite the tissue sample S. Preferably, light source 13 produces ultrafast pulses of light, such as picosecond or femtosecond light pulses. In addition, the light emitted from light source 13 preferably is substantially monochromatic and preferably has a wavelength ranging from about 300 nm to about 850 nm. Examples of lasers suitable for use as light source 13 include picosecond semiconductor lasers with and without the second harmonic generation (SHG), plcosecond YAG or glass lasers with SHG, picosecond nitrogen lasers, picosecond dye lasers, semiconductor laser pump+VAG laser+SHG, semiconductor pumped YAG laser+SHG+dye laser, and picosecond quantum well laser with and without SHG. As will be discussed below, when system 11 is used to detect cancer in human breast tissue, light source 13 preferably emits light at a wavelength of about 310 nm, about 353 nm, or about 530 nm.

System 11 also includes a lens 15 for focusing the light emitted by source 13 onto the tissue sample S, which is mounted on a holder 17. The fluorescent light emitted by tissue sample S is then collected by a lens 19 and passed through a filter 21, which is selective for light of certain predetermined wavelength(s). Filter 21 may be, for example, a narrow band filter having a bandwidth of about 10 nm or a wide band filter having a bandwidth of about 40 nm. Preferably, the wavelength(s) of the fluorescent light passed through filter 21 is (are) different from the wavelength(s) of the light emitted by source 13 so as to ensure the detection of fluorescent light only. Other devices, besides filter 21, which may be used to select only certain, predetermined wavelengths of the fluorescent light include a spectrograph or a zero dispersion spectrometer.

System 11 additionally includes a streak camera 23 for temporally resolving the fluorescent light which passes through filter 21. Preferably, streak camera 23 is capable of operating in either the single pulse or synchroscan modes. Other devices, besides streak camera 21, which may be used to temporally resolve the fluorescent light include an optical Kerr gate, an up-conversion gate, a time-correlated single photon counting instrument, a phase fluorimeter, and an oscilloscope with a fast photodetector.

Figure 11:
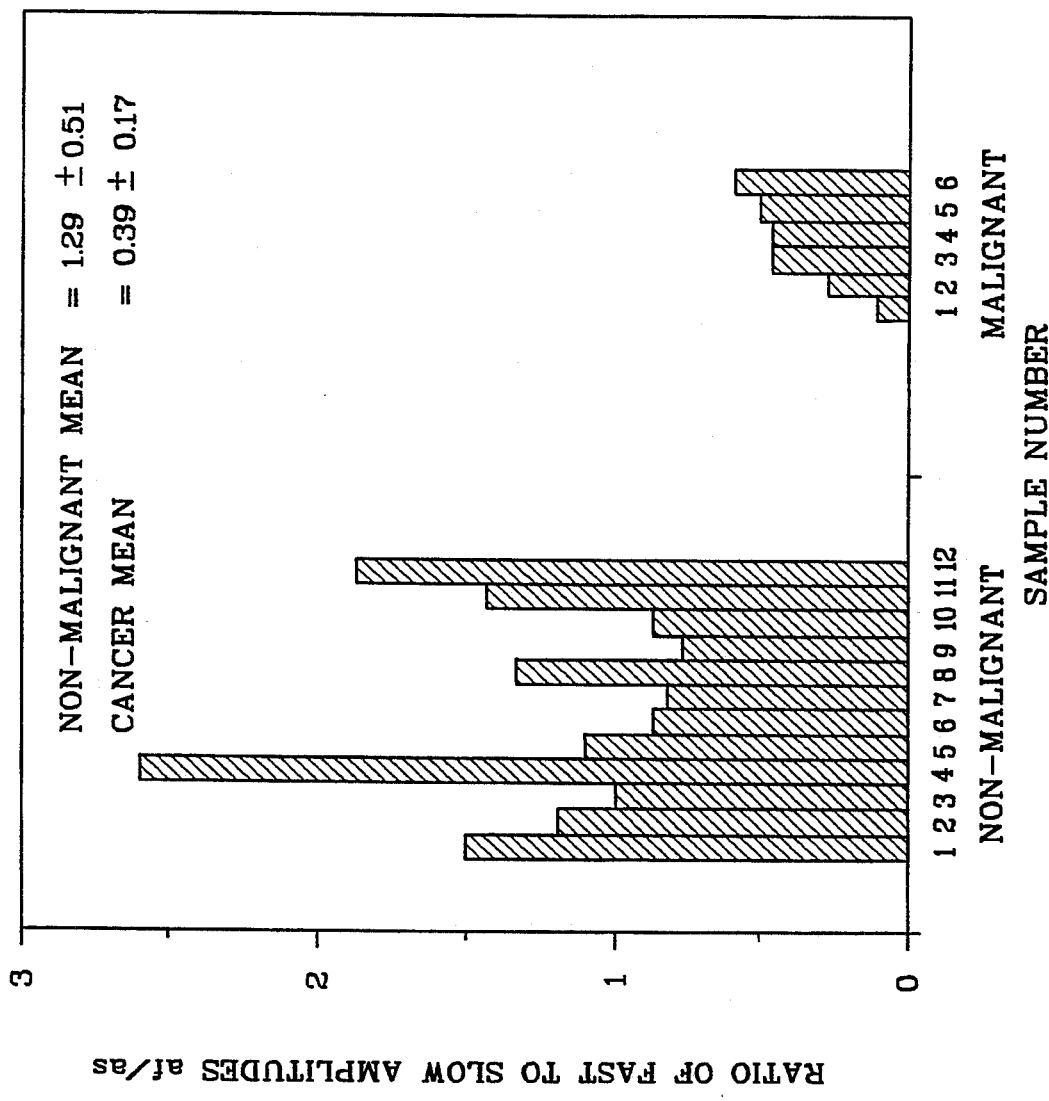
FIG. 11 is a histogram of the ratio of amplitudes of the fast components of fluorescence decay from malignant and non-malignant human breast tissues in the 340 nm emission band following excitation with light at a wavelength of about 310 nm.
Figure 12:
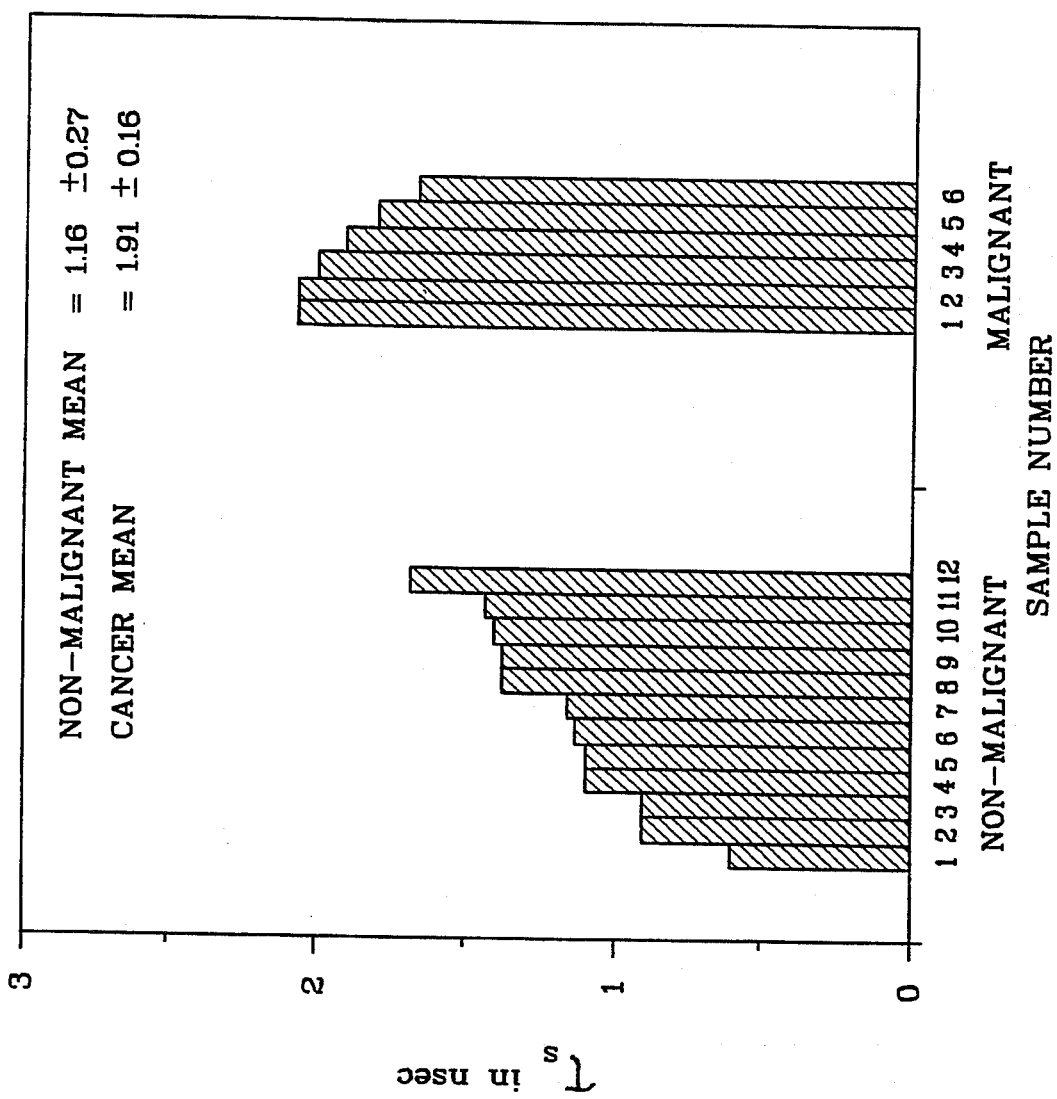
FIG. 12 is a histogram of the slow component of fluorescence lifetimes from malignant and non-malignant human breast tissues in the 340 nm emission band following excitation with light at a wavelength of about 310 nm.

System 11 further includes a camera 25, such as a SIT video camera or a CCD video camera, for converting the temporally resolved light signal from streak camera 23 into a corresponding electrical signal. This signal is then transmitted from camera 23 through a line 27 to a computer 29. Computer 29 processes the signal and compares it to standards obtained from malignant and non-malignant tissues. Such standards may be derived from a histogram of the type shown in FIGS. 11 and 12. The results of the comparison are then displayed on a monitor 31 or printed on hard copy using a printer 33. (As can readily be appreciated, instead of having computer 29 automatically process and compare the time-resolved emission signal to standards, the signal from camera 23 could simply be displayed as a profile either on monitor 31 or using printer 33, in which case the user would visually compare the displayed profile to standards obtained from malignant and non-malignant tissues.)

In analyzing the fluorescence profile of a sample tissue, it is often helpful to look at certain signature features that appear differently in the profiles of malignant tissues than in the profiles of non-malignant tissues. Such signature features include the shape of the fluorescence profile, its relaxation lifetime, and the amplitude(s) (or ratio of amplitudes) of the relaxation component(s). In many instances, these features may be quantified by fitting the fluorescence profile to the equation $I(t) = \Sigma A_i e(-t/\tau_i)$ wherein $\tau$ is dependent upon the number of fluorophores being excited, the number of different environments in which a single fluorophore is being excited, the re-radiation of an excited fluorophore after a time lag, or the like.

Figure 2:
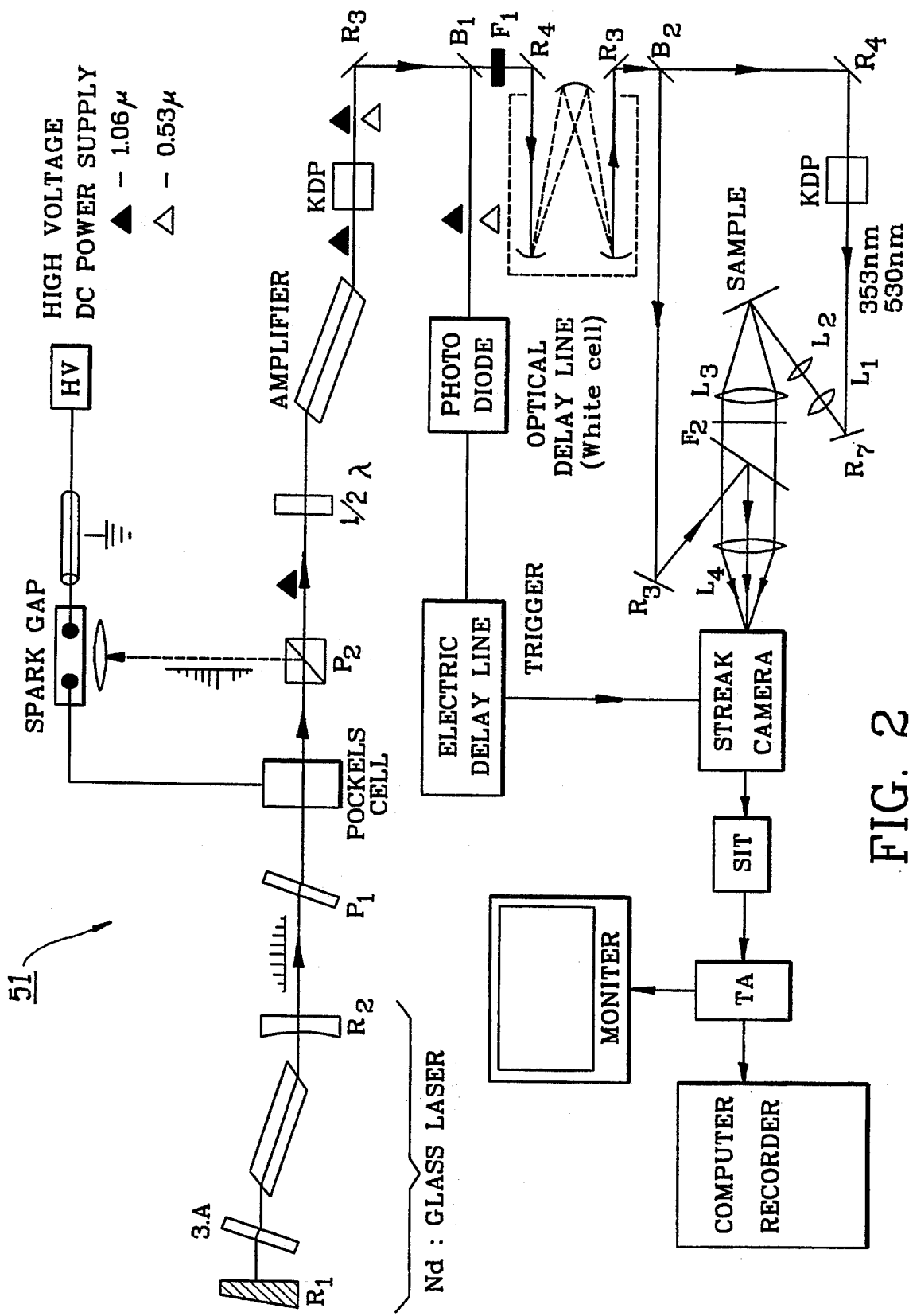
FIG. 2 is a schematic diagram of a second embodiment of a time-resolved fluorescence spectroscopy system which may be used to perform the method of the present invention.
Figure 3A:
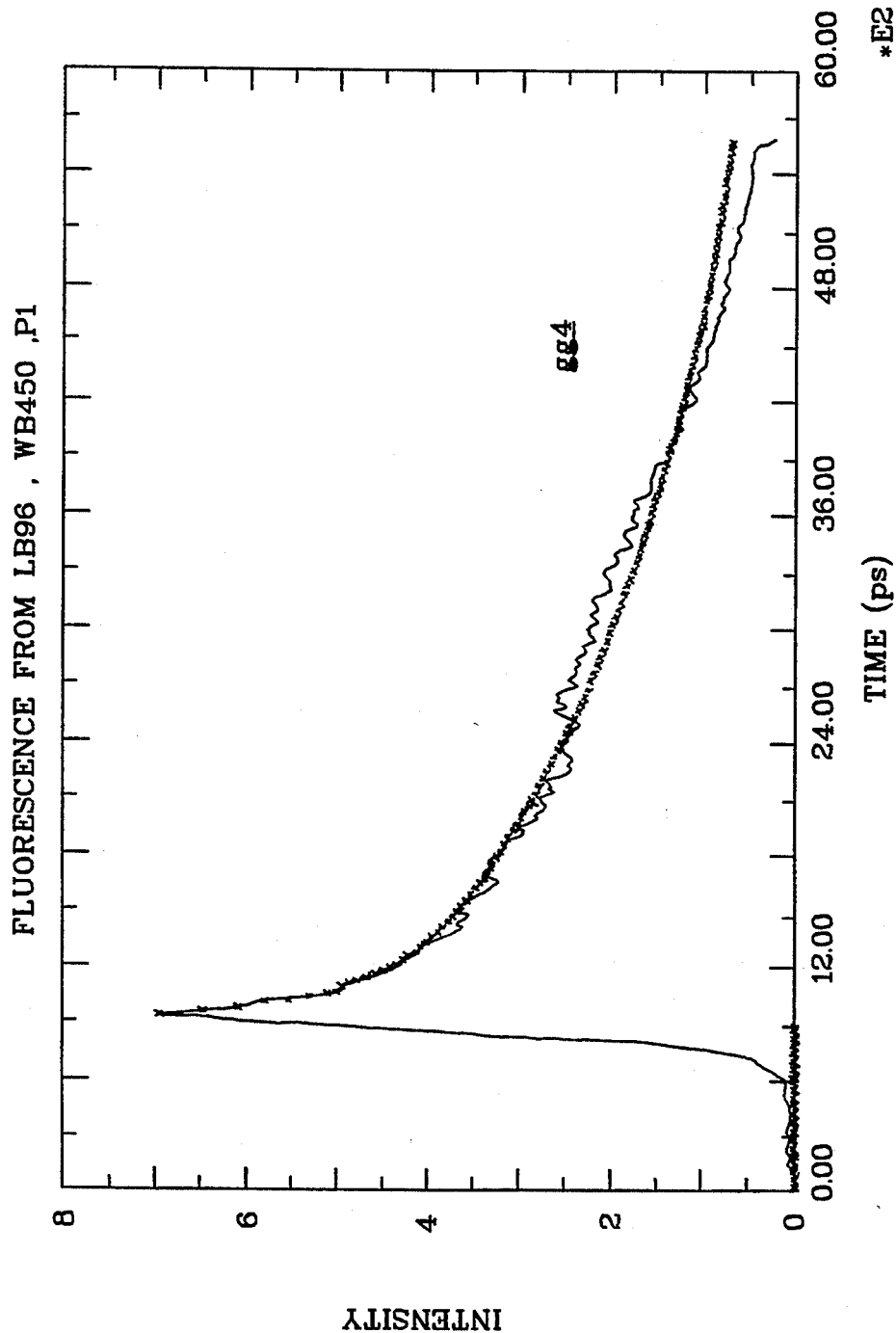
FIGS. 3(a) through 3(d) are time-resolved fluorescence profiles of several malignant human breast tissue samples, the profiles being obtained by exciting the samples with light at a wavelength of about 353 nm and then measuring for a period of time the native fluorescence emitted therefrom at a wavelength of about 450 nm.
Figure 3B:
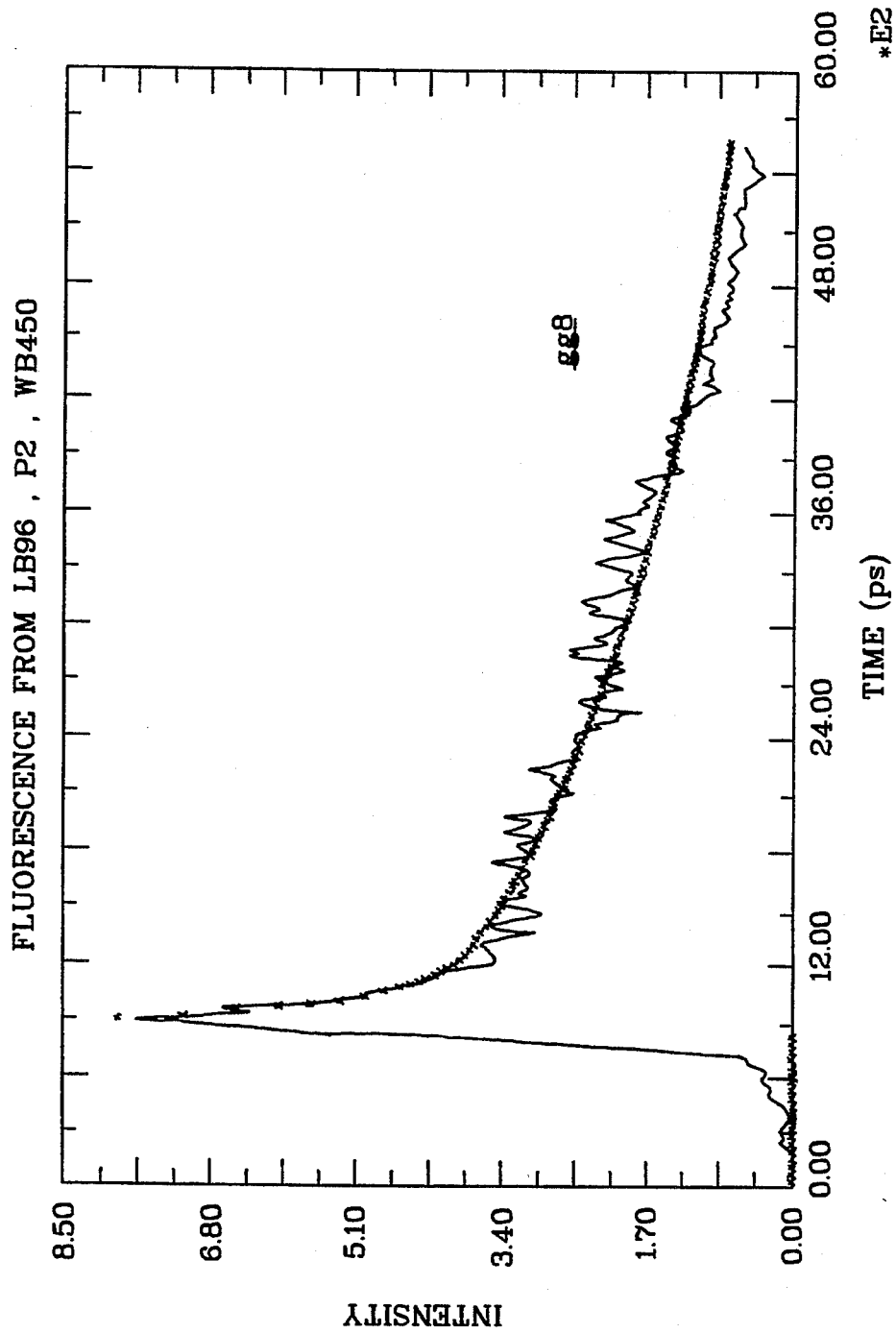
Figure 3C:
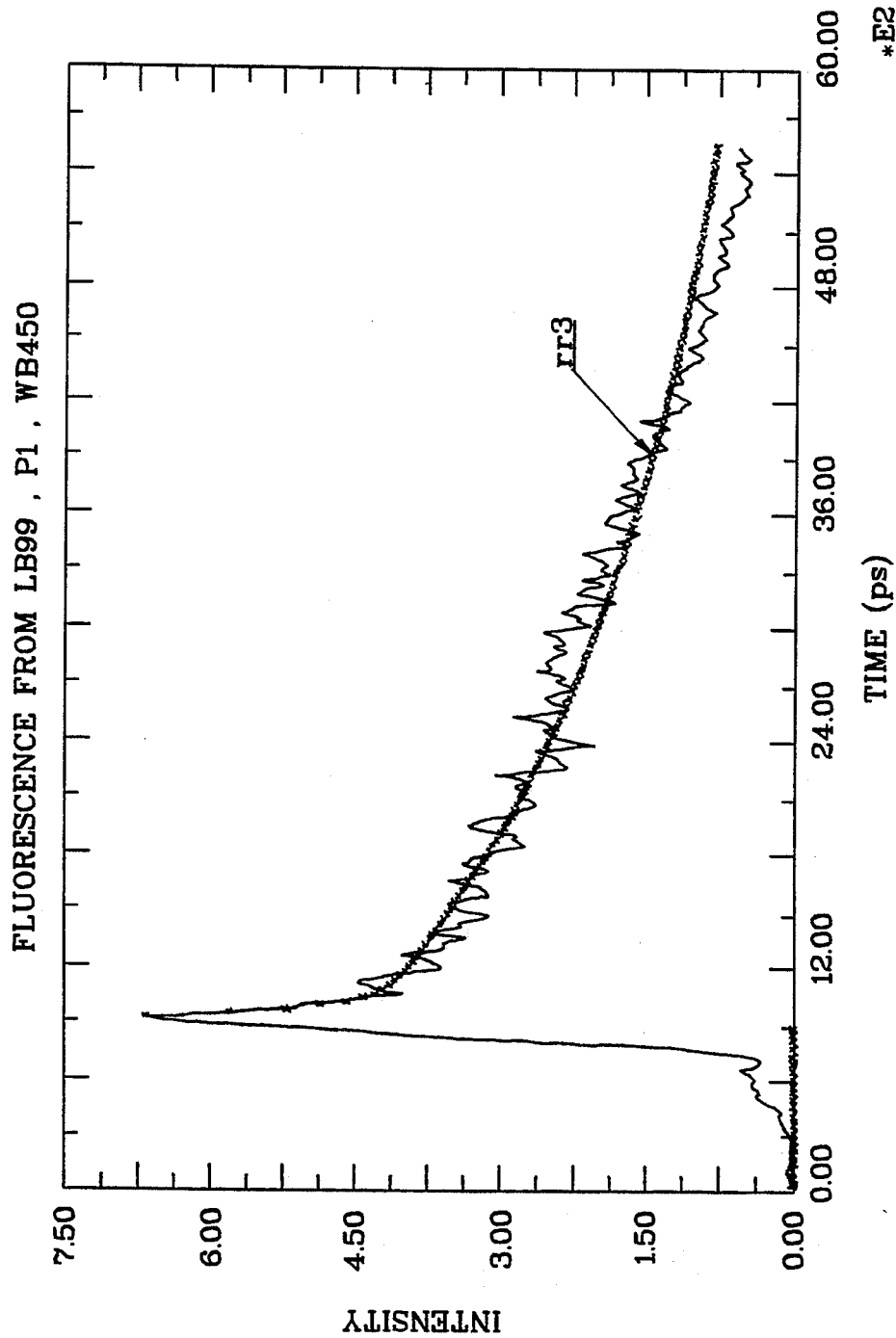
Figure 3D:
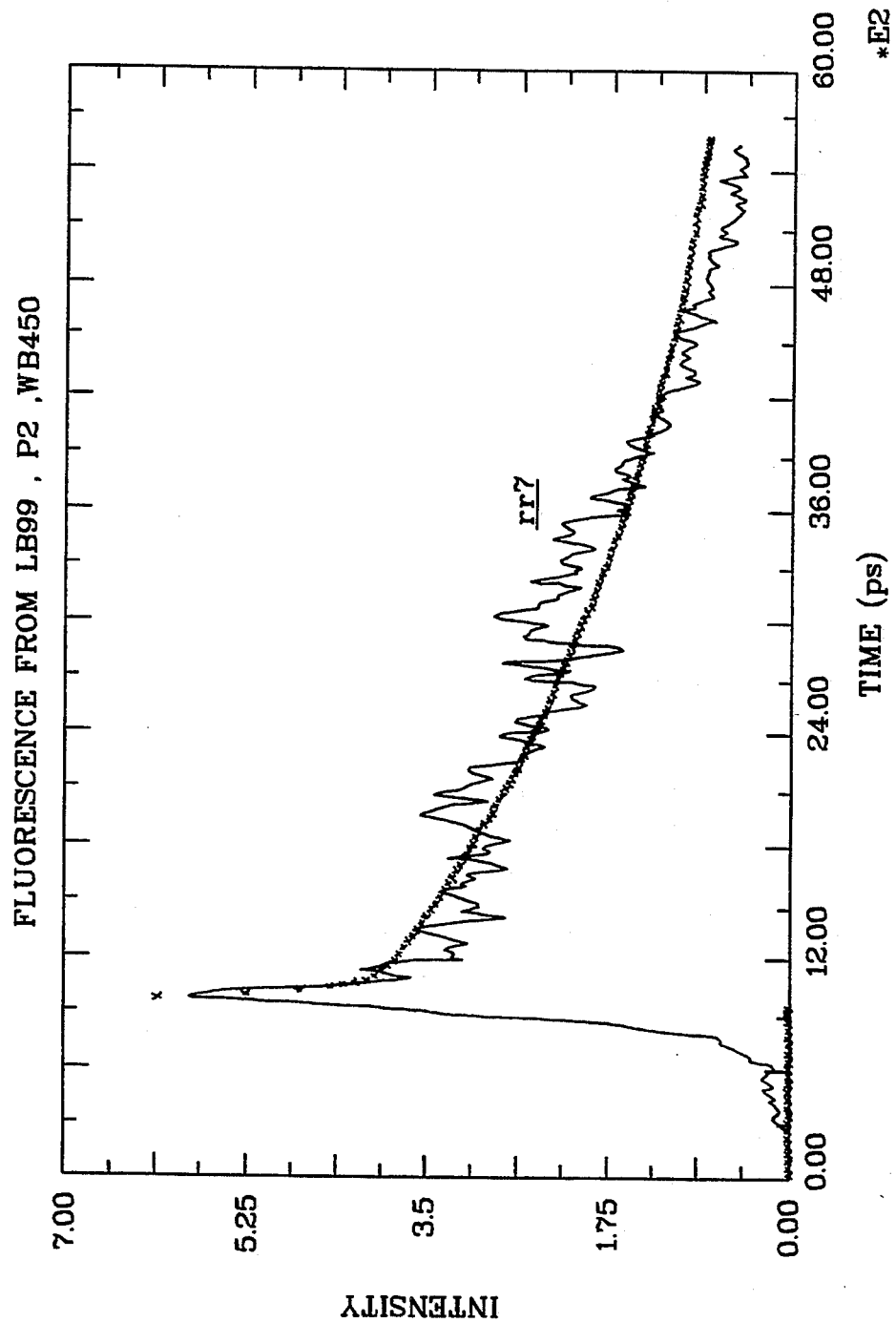
Figure 4A:
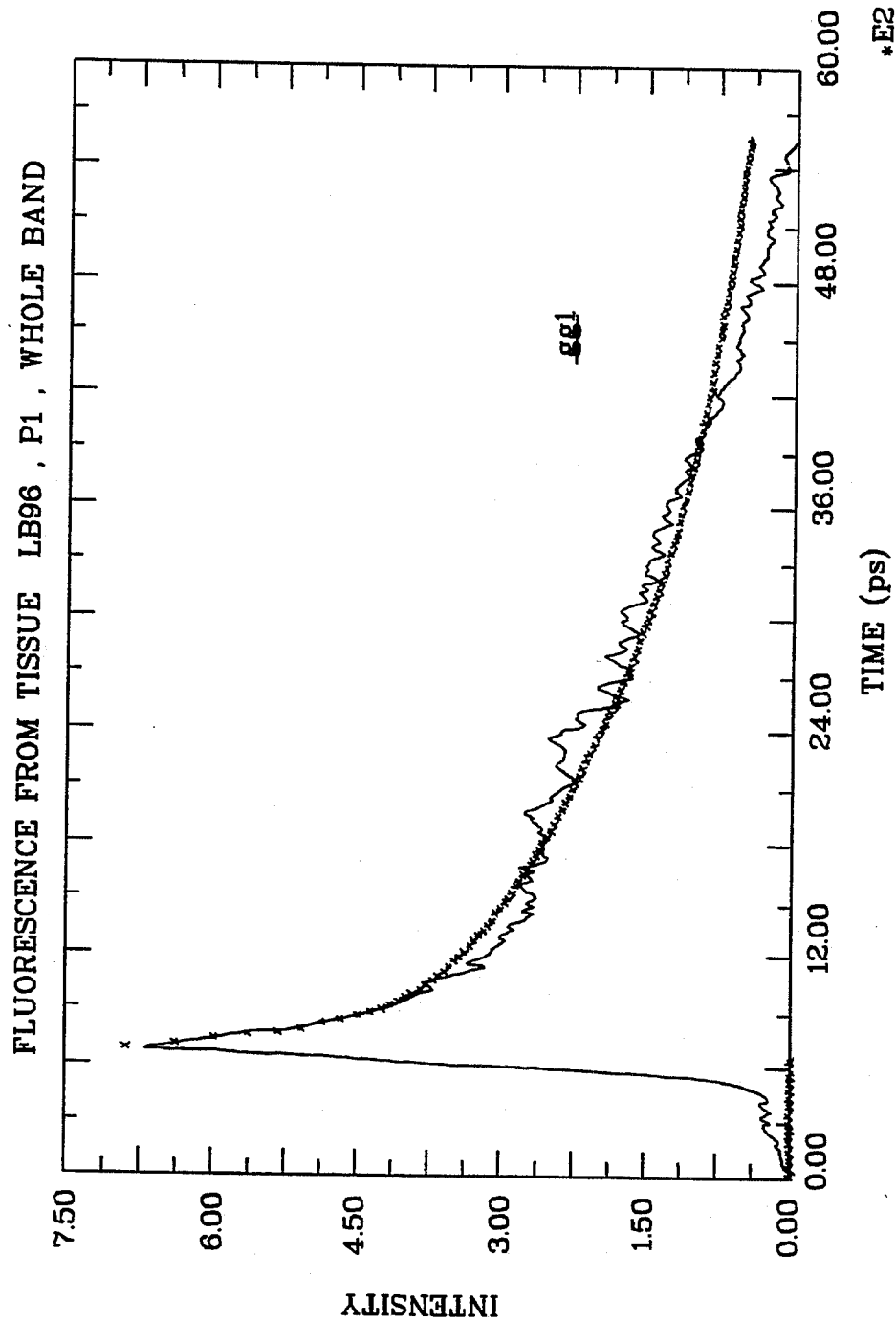
FIGS. 4(a) through 4(d) are time-resolved fluorescence profiles of the malignant human breast tissue samples of FIGS. 3(a) through 3(d), respectively, the profiles being obtained by exciting the samples with light at a wavelength of about 353 nm and then measuring for a period of time the total native fluorescence emitted therefrom.
Figure 4B:
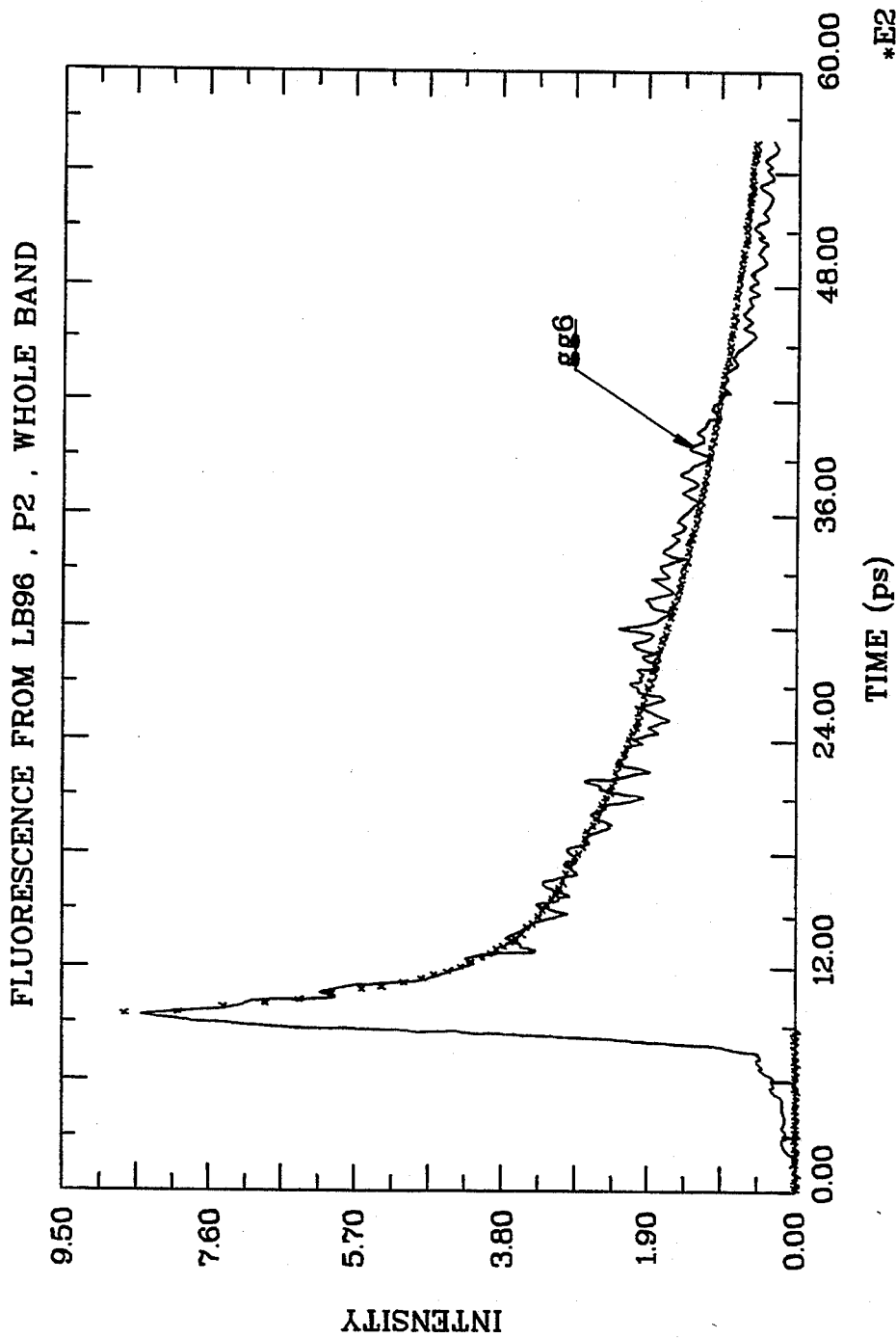
Figure 4C:
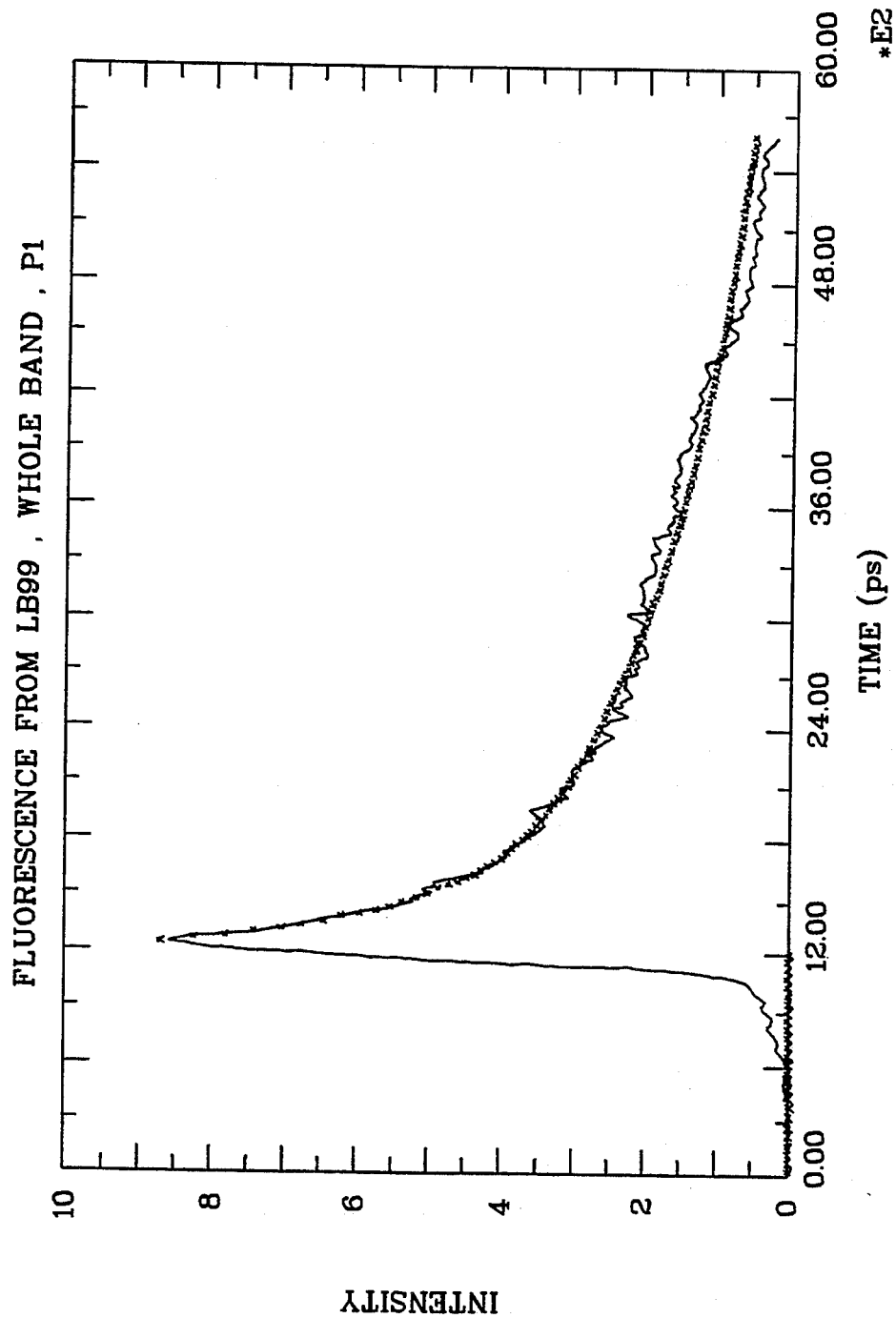
Figure 4D:
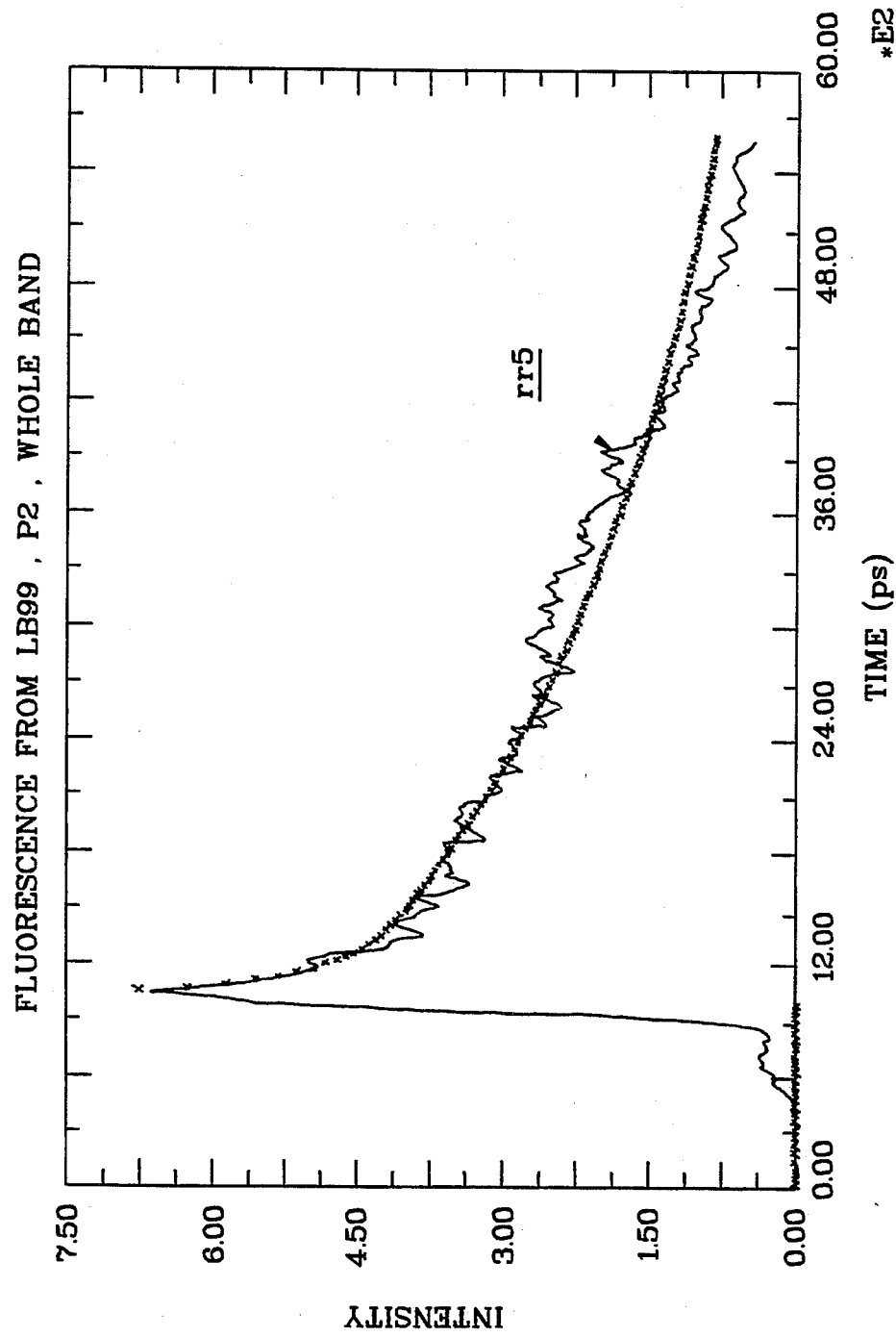
Figure 5B:
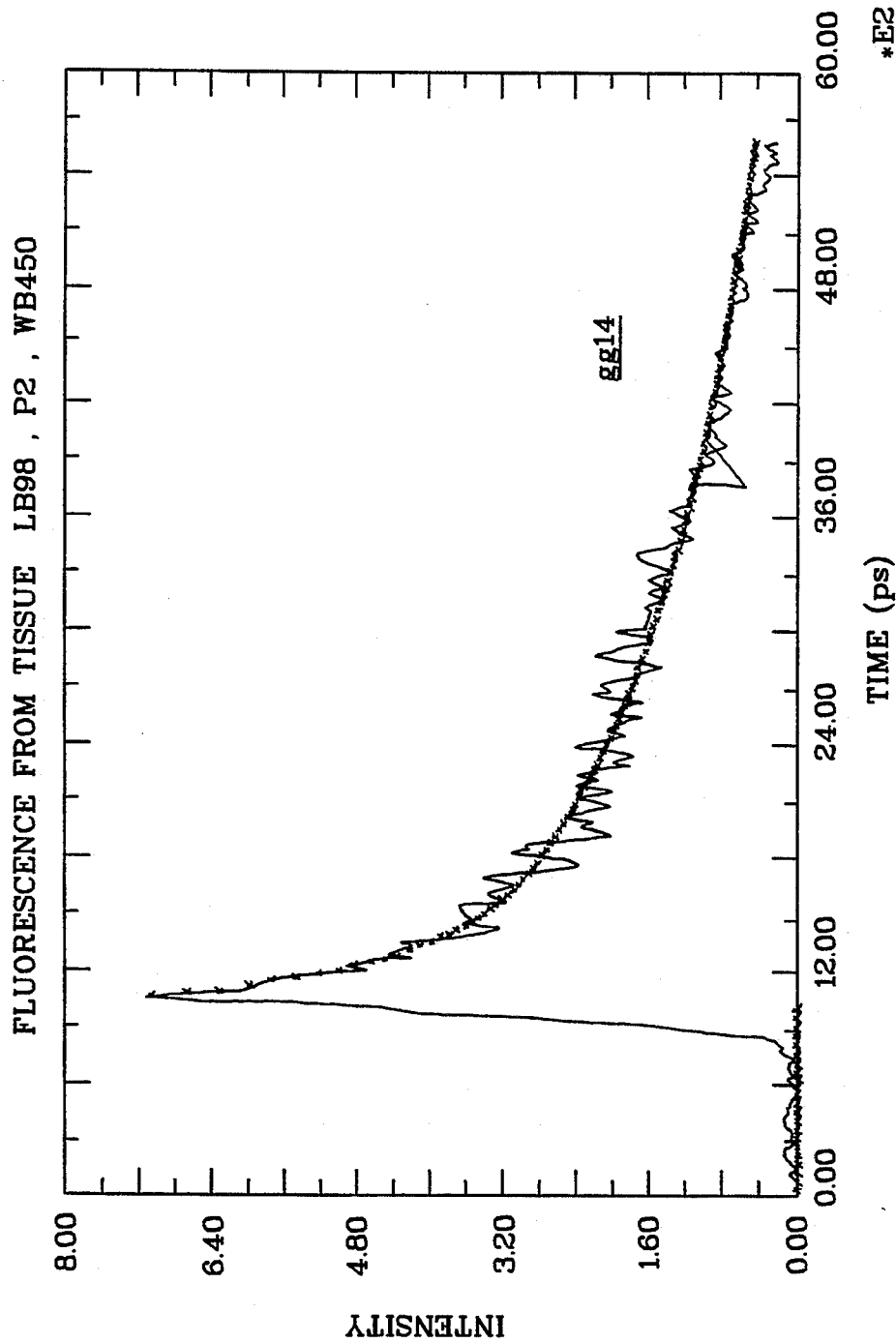
Figure 6A:
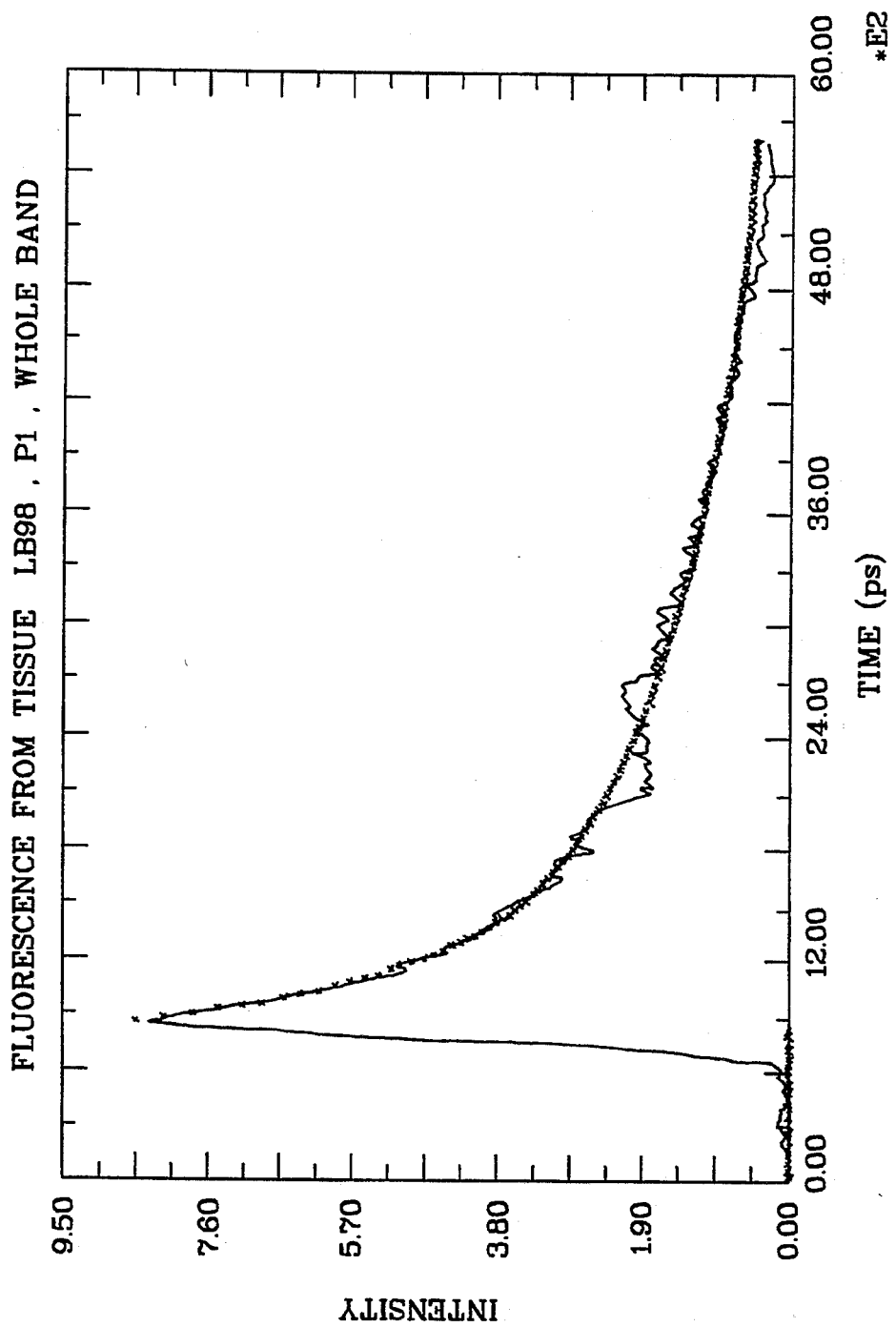
FIGS. 6(a) and 6(b) are time-resolved fluorescence profiles of the two benign human breast tumor tissue samples of FIGS. 5(a) and 5(b), the profiles being obtained by exciting the samples with light at a wavelength of about 353 nm and then measuring for a period of time the total native fluorescence emitted therefrom.
Figure 6B:
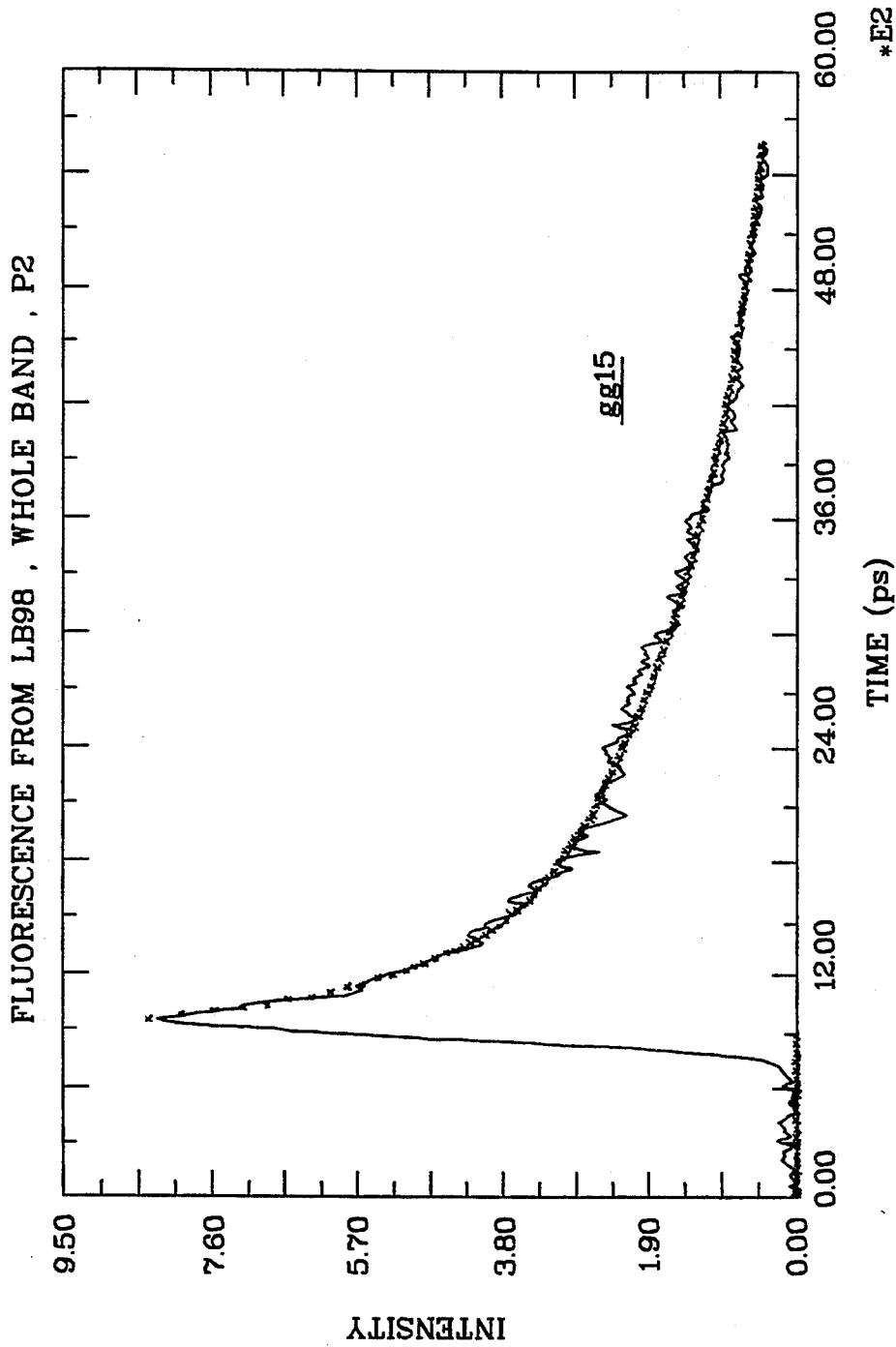
Figure 7:
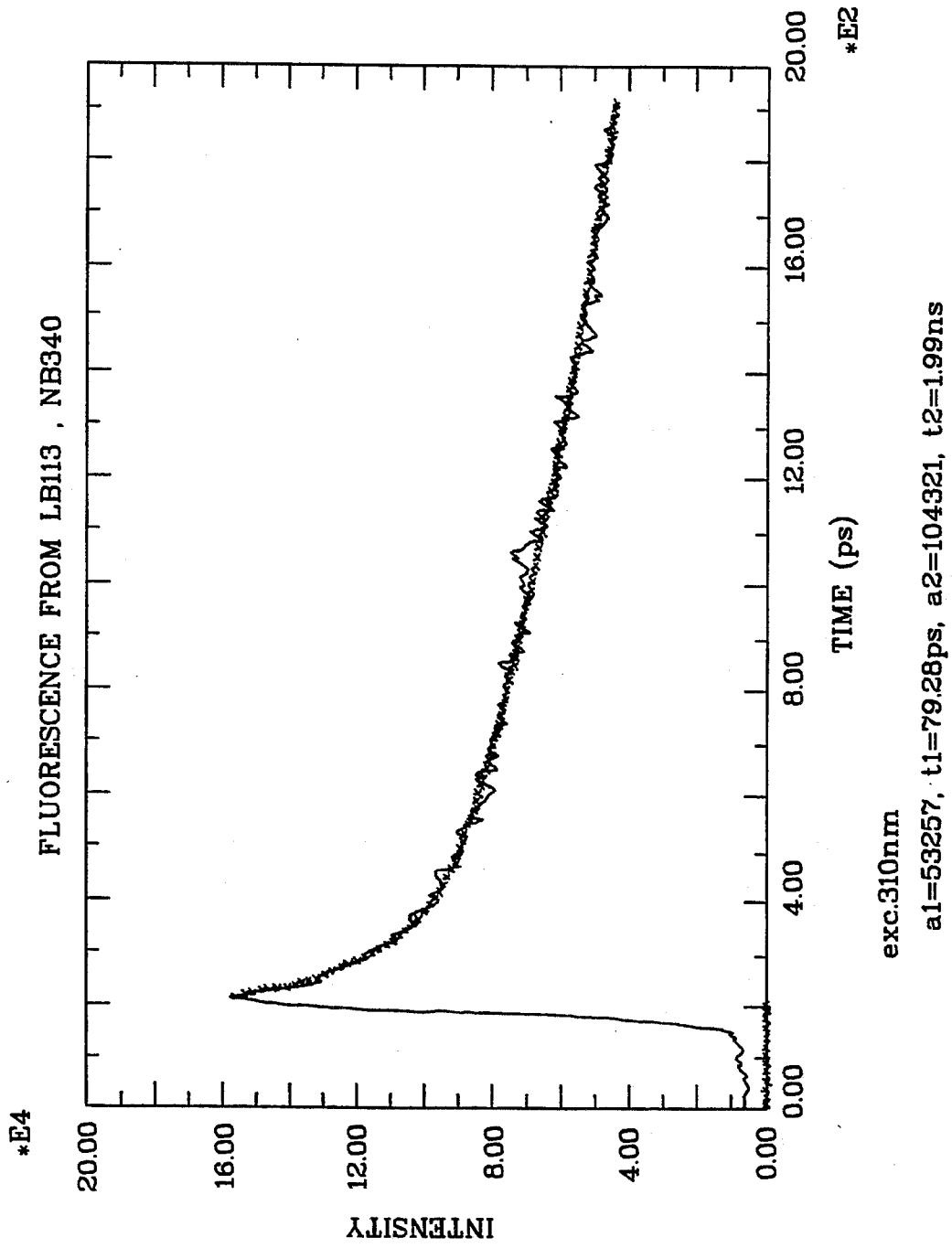
FIG. 7 is a representative time-resolved fluorescence profile of malignant human breast tissue sample, the profile being obtained by exciting the sample with light at a wavelength of about 310 nm and then measuring for a period of time the native fluorescence emitted therefrom at a wavelength of about 340 nm.
Figure 8:
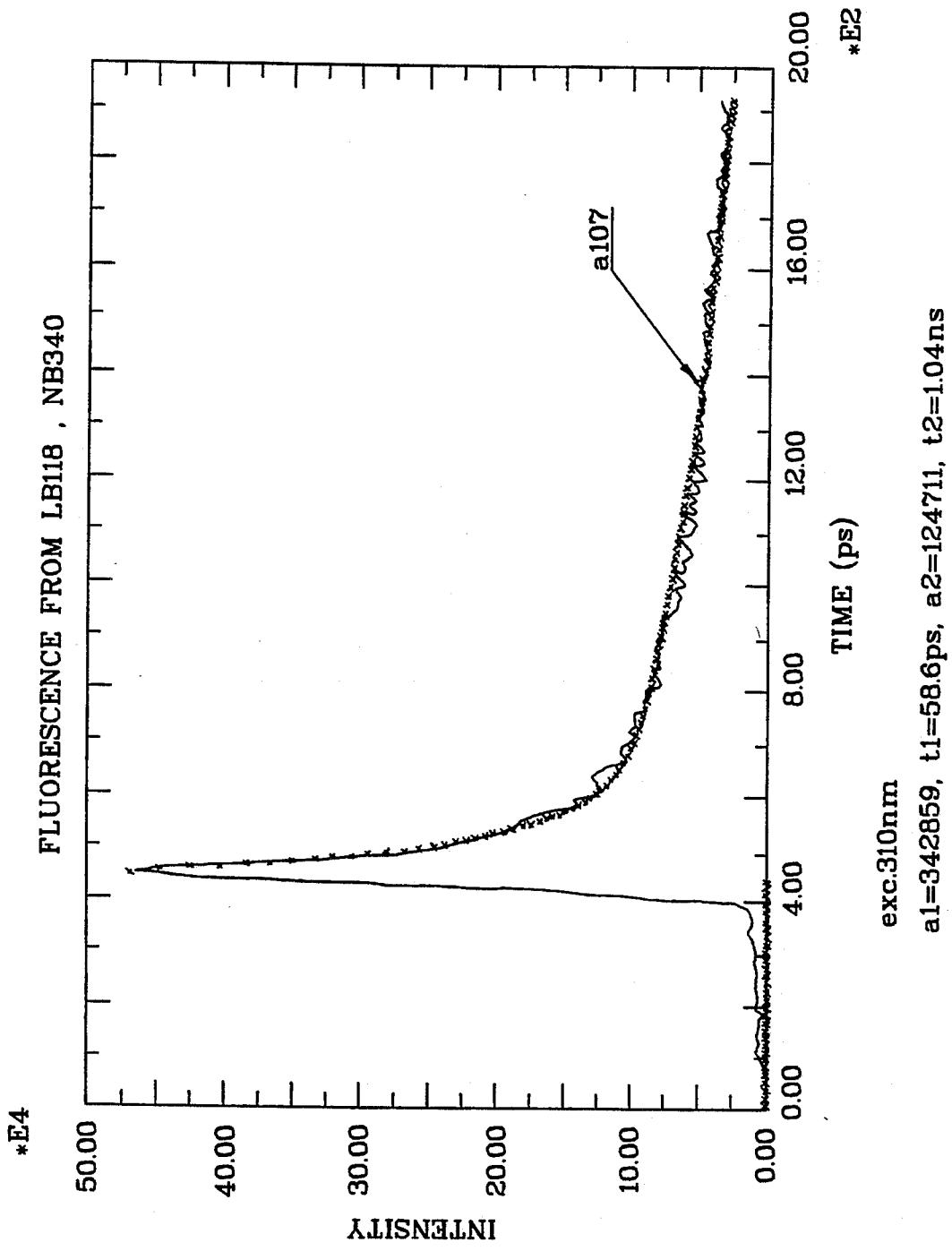
FIG. 8 is a representative time-resolved fluorescence profile of a benign human breast tumor tissue sample, the profile being obtained by exciting the sample with light at a wavelength of about 310 nm and then measuring for a period of time the native fluorescence emitted therefrom at a wavelength of about 340 nm.
Figure 9:
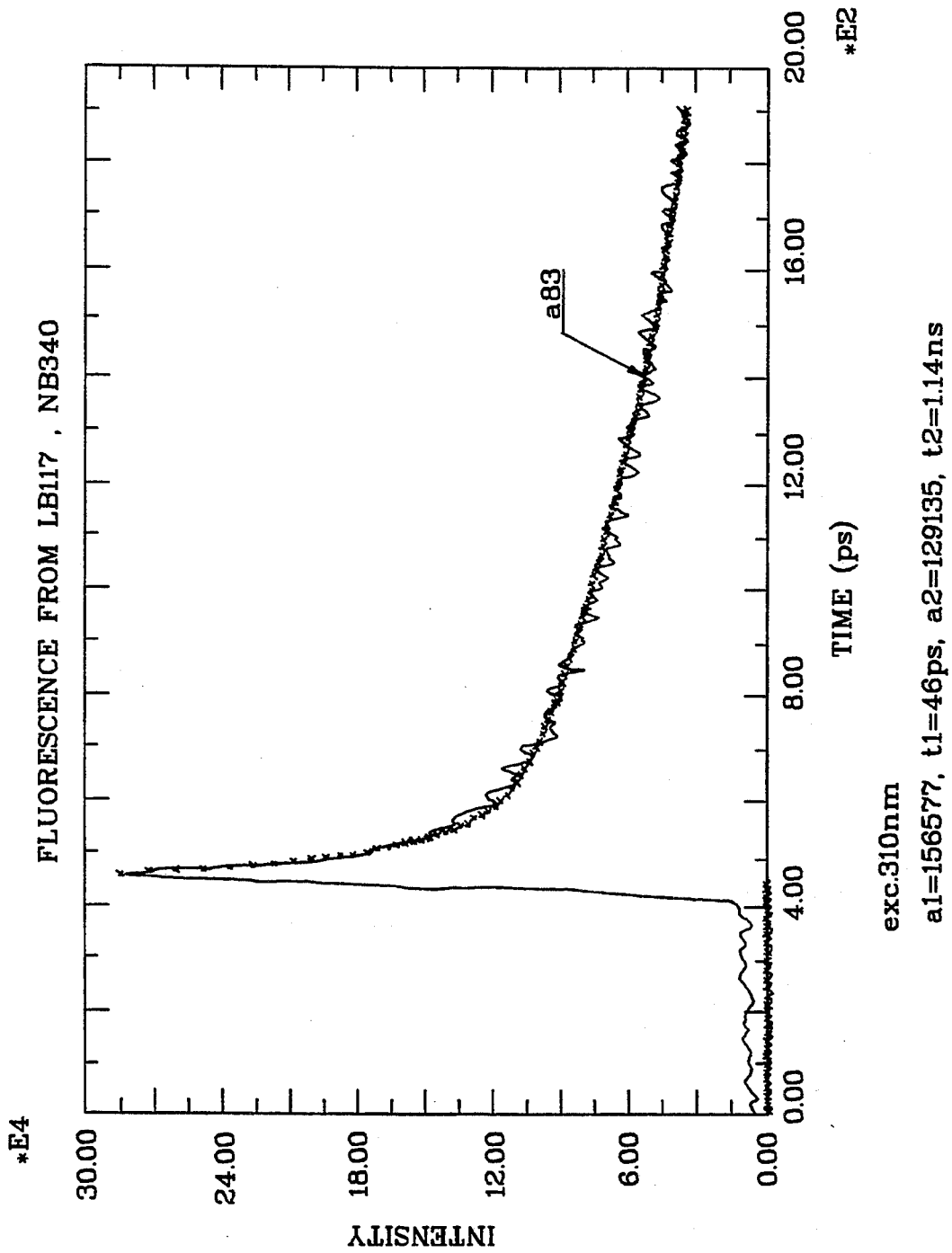
FIG. 9 is a representative time-resolved fluorescence profile of a benign human breast tissue sample, the profile being obtained by exciting the sample with light at a wavelength of about 310 nm and then measuring the native fluorescence emitted therefrom at a wavelength of about 340 nm.
Figure 10:
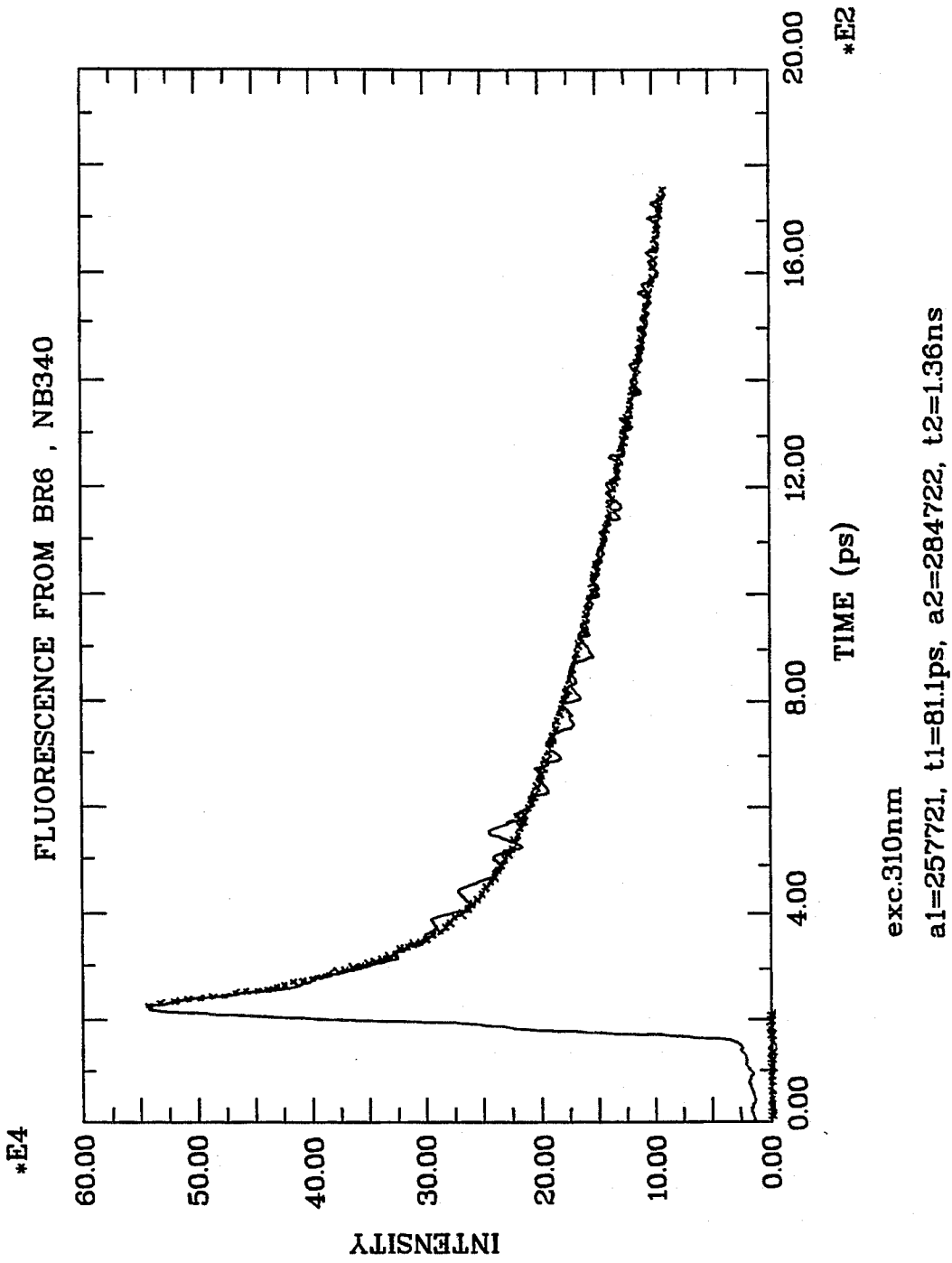
FIG. 10 is a representative time-resolved fluorescence profile of a normal human breast tissue sample, the profile being obtained by exciting the sample with light at a wavelength of about 310 nm and then measuring the native fluorescence emitted therefrom at a wavelength of about 340 nm.

A second embodiment of a time-resolved fluorescence spectroscopy system constructed according to the teachings of the present invention is shown in FIG. 2, the system being represented generally by reference numeral 51.

EXAMPLE 1

Time-resolved fluorescence profiles for a malignant human breast tissue sample and a normal human breast tissue sample were obtained and fitted to the equation $I(t) = A_1 e(-t/\tau_1) + A_2 e(-t/\tau_2)$ using the general set-up of system 51. The excitation wavelength; used was about 530 nm, and the native fluorescence emitted from the tissue samples was measured after passage through either a wide band 600 nm filter (WB600) or no filter (WHOLE BAND). The results are set forth below in Table 1.

TABLE 1

| SAMPLE | WHOLE BAND | | WB600 | |
|---|---|---|---|---|
| | $\tau_1$ $A_1$ | $\tau_2$ $A_2$ | $\tau_1$ $A_1$ | $\tau_2$ $A_2$ |
| Normal Human Breast Tissue | 210 ps 80.6 | 1.7 ns 137.8 | 190 ps 62 | 1.6 ns 145 |
| Malignant Human Breast Tumor Tissue | 170 ps 112 | 1.6 ns 120 | 110 ps 52.8 | 1.6 ns 178 |

As can be seen, the fast component ($\tau_1$) of the malignant human breast tissue Is considerably faster than the fast component ($\tau_1$) of the normal human breast tissue (100 ps rs. 200 ps) whereas the slow components ($\tau_2$) of the two tissues are about the same (approx. 1.6 ns). Other differences In the respective spectra include variations in amplitudes $A_1$ and $A_2$ of the malignant and normal tissues.

EXAMPLE 2

Time-resolved fluorescence profiles for various malignant human breast tissue samples and benign human breast tumor tissue samples were obtained using the general set-up of system 51 and fitted to the equation $I(t) = A_1 e(-t/\tau_1) + A_2 e(-t/\tau_2)$. The excitation wavelength used gas about 350 nm. and the fluorescence emitted from the tissue samples was measured after passage through either a wide band 400 nm filter (WB400), a wide band 450 nm filter (WB450), a wide band 500 nm filter (WB500) or no filter (WHOLE BAND). The results are set forth below in Table 2. (In addition, the fluorescence profiles for each of the tissue samples listed below using either a side band 450 nm filter or no filter are shown in FIGS. 3 through 6.)

TABLE 2

| SAMPLE | WHOLE BANK | | WB400 | | WB450 | | WB500 | |
|---|---|---|---|---|---|---|---|---|
| | $\tau_1$ $A_1$ | $\tau_2$ $A_2$ | $\tau_1$ $A_1$ | $\tau_2$ $A_2$ | $\tau_1$ $A_1$ | $\tau_2$ $A_2$ | $\tau_1$ $A_1$ | $\tau_2$ $A_2$ |
| Malignant Tumor Tissue Sample LB96 p1 | 120 ps 2.6 | 2.3 ns 4.3 | 117 ps 2.6 | 2.5 ns 5.1 | 117 ps 2.2 | 2.5 ns 4.8 | 117 ps 2.4 | 2.4 ns 5.4 |
| Malignant Tumor Tissue Sample LB96 p2 | 144 ps 4.6 | 2.3 ns 4.2 | 80 ps 3.5 | 2.5 ns 5.2 | 99 ps 3.5 | 2.7 ns 4.4 | 123 ps 2.4 | 2.7 ns 3.8 |
| Malignant Tumor Tissue Sample LB99 p1 | 206 ps 4 | 2.2 ns 4.7 | 79 ps 2.7 | 2.6 ns 6.6 | 52 ps 2.3 | 2.77 ns 4.3 | 76 ps 2.8 | 2.8 ns 4.7 |

TABLE 2-continued

| SAMPLE | WHOLE BANK | | WB400 | | WB450 | | WB500 | |
|---|---|---|---|---|---|---|---|---|
| | $\tau_1$ $A_1$ | $\tau_2$ $A_2$ | $\tau_1$ $A_1$ | $\tau_2$ $A_2$ | $\tau_1$ $A_1$ | $\tau_2$ $A_2$ | $\tau_1$ $A_1$ | $\tau_2$ $A_2$ |
| Malignant Tumor Tissue Sample LB99 p2 | 83 ps 2 | 2.7 ns 4.8 | 82 ps 2.9 | 2.8 ns 5.7 | 42 ps 2 | 3 ns 4.2 | 68 ps 2.3 | 3 ns 4 |
| Benign Tumor Tissue Sample LB98 p1 | 288 ps 4.3 | 2.1 ns 4.3 | — | — | 236 ps 3.9 | 2.1 ns 5 | 226 ps 3.4 | 1.6 ns 4.4 |
| Benign Tumor Tissue Sample LB98 p2 | 206 ps 3.6 | 2.2 ns 4.9 | — | — | 189 ps 3.1 | 2.2 ns 4 | 285 ps 3 | 2.2 ns 3.1 |

As can be seen, the fast components ($\tau_1$) of the malignant tissues are less than about 150 ps while the fast components ($\tau_1$) of the benign tumor tissues are greater than 200 ps. In addition. In addition, the slow components ($\tau_2$) of the malignant tissues are greater than 2.4 ns whereas the slow components ($\tau_2$) of the benign tumor tissues are less than 2.4 ns. Consequently, using these signature differences, one can accurately characterize tumorous tissue as being either malignant or benign.

EXAMPLE 3

Ultrafast 100 fs laser pulses (repetition rate —82 MHz; wavelength —620±7 nm; beam diameter —3 mm) of 0.1 nJ per pulse were generated from a colliding pulse mode-locked dye laser system. These laser pulses were amplified by a sulphur rhodamine gain medium pumped by a copper vapor laser at 6.5 kHz. Laser pulses at 310 wavelength were obtained by focusing the 620 nm beam into a KDP crystal to generate the second harmonic. Breast tissue samples were put into quartz cells and excited at 310 nm. The pulse energy at the sample site was 0.5 uJ and the results were an average of a few tens of thousand pulses. The fluorescence was collected into a synchroscan streak camera with a temporal resolution of 16 ps. The sampling volume was a few hundred microns in area and 1 mm in depth. The tissue fluorescence was collected at the emission band of 340 nm ±5 nm and 440 nm ±5 nm using narrow band filters. Time-resolved fluorescence measurements were performed on 18 samples of human breast tissue from different sources —6 malignant tumors, 5 benign tissues, 5 normal tissues, and 2 benign tumors. The profiles were then fitted to the equation $I(t) = A_1 e(-t/\tau_1) + A_2 e(-t/\tau_2)$. The results are set forth below in Table 3. (In addition, the fluorescence profiles for representative malignant, benign tumor, benign tissue and normal samples are shown in FIGS. 7 through 10, respectively.)

TABLE 3

| SAMPLE | 340 nm | | | 440 nm | | |
|---|---|---|---|---|---|---|
| | $\tau_1$ | $\tau_2$ | $A_1/A_2$ | $\tau_1$ | $\tau_2$ | $A_1/A_2$ |
| Benign Tumor Tissue Sample LB 114 | 49 | 0.894 | 1.52 | 79 | 1.93 | 0.21 |
| Benign Tissue Sample LB 117 | 46 | 1.14 | 1.2 | 69 | 1.22 | 0.97 |
| Benign Tumor Tissue Sample LB 118 | 59 | 0.889 | 2.58 | 65 | 1.41 | 0.81 |
| Benign Tissue Sample LB 119 | 60 | 1.1 | 1.04 | 80 | 1.05 | 0.74 |
| Benign Tissue Sample LB 155 | 50 | 1.34 | 1.1 | 72 | 1.6 | 0.5 |
| Benign Tissue Sample LB 156 | 60 | 1.1 | 0.9 | — | — | — |
| Benign Tissue Sample LB 163 | 102 | 1.12 | 0.85 | 49 | 1.4 | 0.5 |
| Normal Tissue Sample BR1 | 103 | 1.34 | 1.35 | — | — | — |
| Normal Tissue Sample BR3 | 75 | 1.65 | 0.78 | — | — | — |
| Normal Tissue Sample BR6 | 81 | 1.36 | 0.9 | — | — | — |
| Normal Tissue Sample BR7 | 114 | 0.616 | 1.47 | — | — | — |
| Normal Tissue Sample BR11 | 85 | 1.38 | 1.83 | 89 | 1.7 | 0.86 |
| Malignant Tissue Sample LB109 | 54 | 2.06 | 0.46 | 39 | 1.64 | 0.2 |
| Malignant Tissue Sample LB110 | 65 | 2.06 | 0.11 | — | — | — |
| Malignant Tissue Sample LB113 | 79 | 1.99 | 0.5 | 66.8 | 1.35 | 1.8 |
| Malignant Tissue Sample LB148 | 110 | 1.93 | 0.26 | — | — | — |
| Malignant Tissue Sample LB162 | 20.5 | 1.64 | 0.46 | 52 | 1.7 | 0.66 |
| Malignant Tissue Sample LB169 | 77 | 1.8 | 0.56 | 93 | 1.8 | 0.74 |

As can be seen, the measurements taken using the 340 nm filter show significant differences in the fluorescence lifetimes and amplitudes of the malignant tissue samples as compared to the non-malignant tissue samples (i.e., benign tumor, benign tissue, and normal samples). For example, the slow component ($\tau_2$) for the non-malignant tissue samples is typically less than about 1.6 ns whereas the slow component ($\tau_2$) for the malignant tissue samples is typically greater than about 1.6 ns. (This data is expressed in the form of a histogram in FIG. 11, where it can be seen that the mean for the slow component of the non-malignant tissue samples is about 1.16±0.27 ns whereas the mean for the slow component of the malignant tissue samples is about 1.91+0.16 ns.) In addition, the ratio of fast to slow amplitudes ($A_1/A_2$) for the non-malignant tissue samples is typically greater than about 0.85 whereas the ratios fast to slow amplitudes ($A_1/A_2$) for the malignant tissues is typically less than about 0.6. (This data is also expressed in the form of a histogram in FIG. 12, where it can be seen that the mean for the ratio of amplitudes for the non-malignant tissue samples is about 1.29±0.51 whereas the mean for the ratio of amplitudes for the malignant tissue samples is about 0.39±0.17.)

In contrast with the series of measurements taken at about 340 nm, the measurements taken at 440 nm do not appear to show any significant differences in the fluorescence lifetimes or amplitudes of the malignant tissue samples as compared to the non-malignant tissue samples.

As can readily be appreciated, the above examples are not intended to be limiting, and it is envisioned that additional differences in the time-resolved fluorescence spectra of malignant human breast tissues and non-malignant human breast tissues may be found by using different excitation and/or emission wavelengths. Some guidance for selecting the appropriate excitation and/or emission wavelengths may be derived from those excitation and/or emission wavelengths which produce a discernible difference in the steady-state fluorescence spectra of malignant human breast tissues and non-malignant human breast tissues. (This approach, however, is not foolproof as can be seen above from the results of the measurements taken at 440 nm.).

Figure 13:
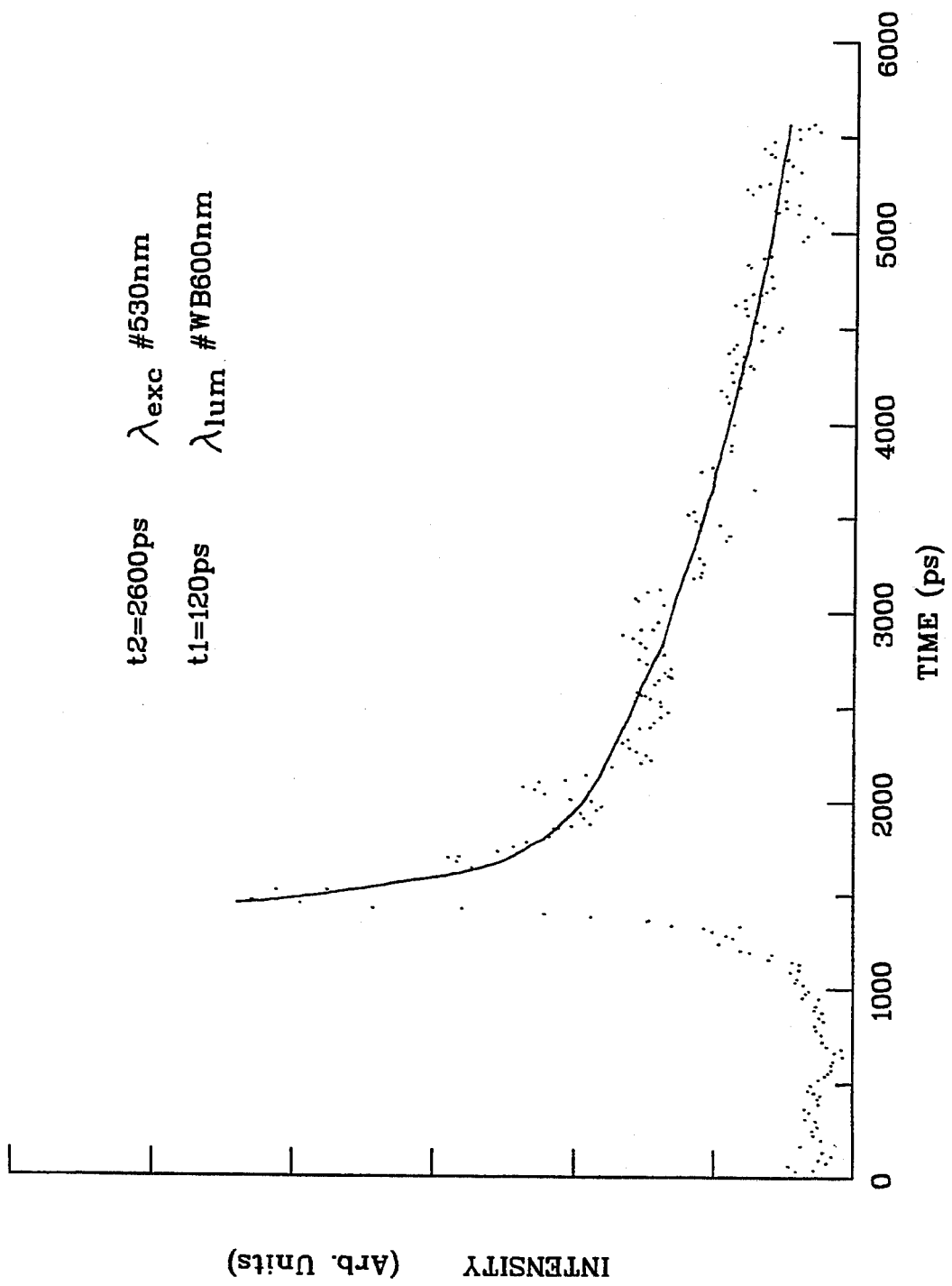
FIG. 13 is a time-resolved fluorescence profile of a malignant human lung tissue sample, the profile being obtained by exciting the sample with light at a wavelength of about 530 nm and then measuring the native fluorescence emitted therefrom at a wavelength of about 600 nm.
Figure 14:
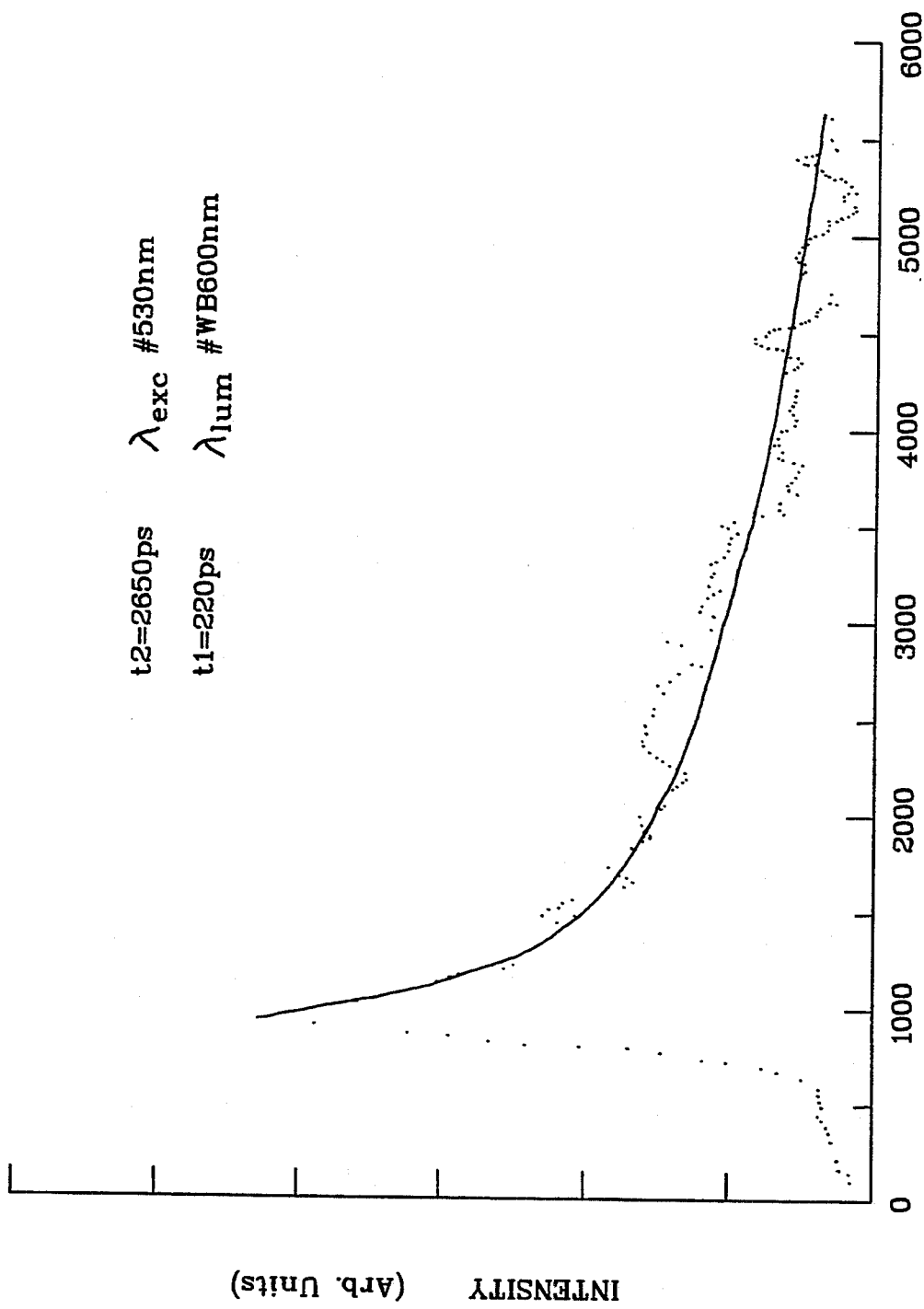
FIG. 14 is a time-resolved fluorescence profile of a normal human lung tissue sample, the profile being obtained by exciting the sample with light at a wavelength of about 530 nm and then measuring the native fluorescence emitted therefrom at a wavelength of about 600

As can also be appreciated, the approach discussed above can also be applied to detecting cancer in tissues other than human breast tissue. For example, FIGS. 13 and 14 illustrate the time-resolved fluorescence profiles of a normal human lung tissue sample and a cancerous human lung tissue sample, respectively, the profiles being obtained by exciting the respective samples with light at a wavelength of about 530 nm and then measuring the native fluorescence emitted therefrom at a wavelength of about 600 nm, When the profiles were fitted to the double exponential equation described above, it was observed that the fast component ($\tau_1$) of the malignant tissue was appreciably faster (120 ps rs. 220 ps) than that of the normal tissue.

Figure 15:
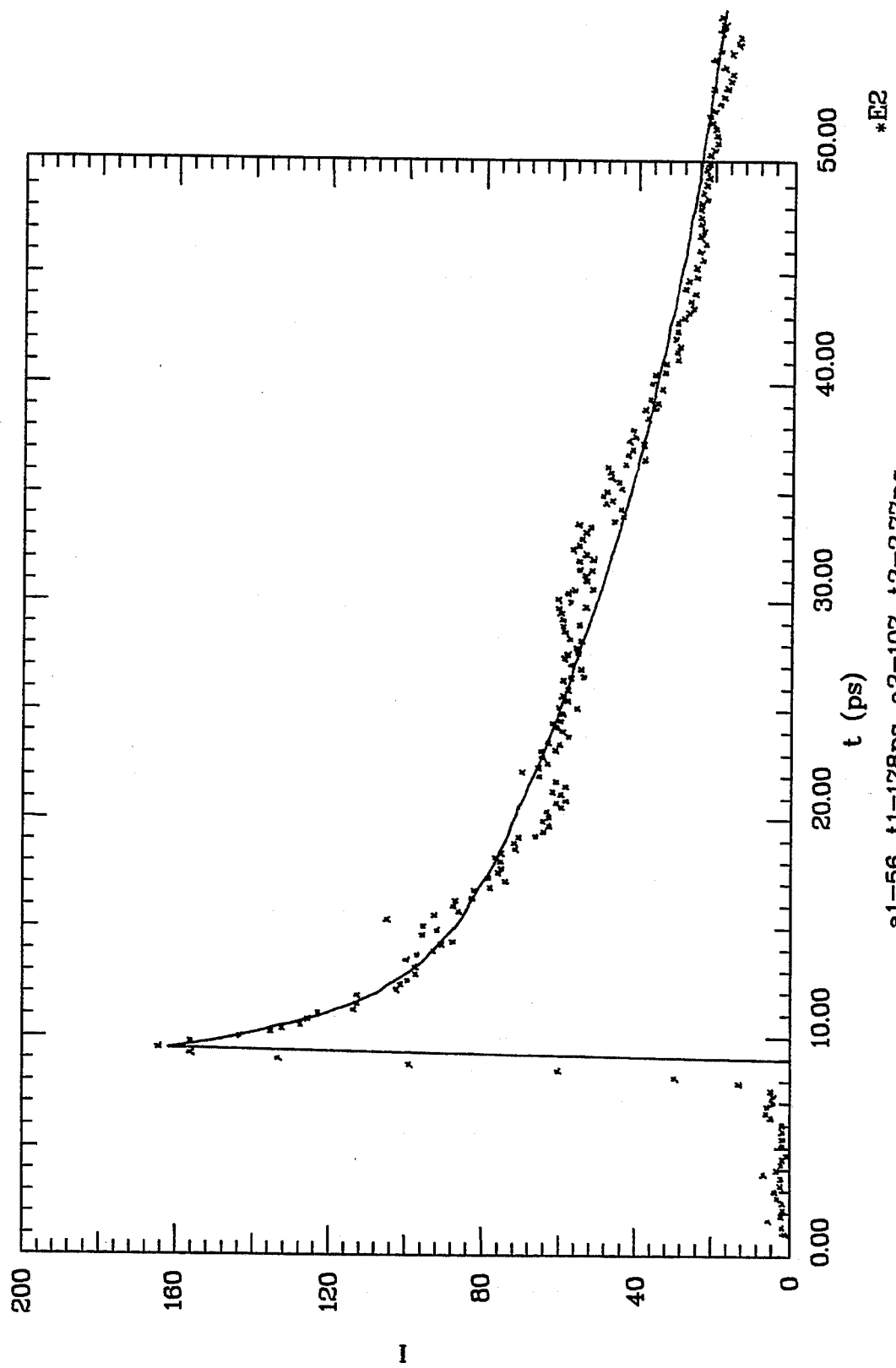
FIG. 15 is a time-resolved fluorescence profile of a malignant human ovarian tissue sample, the profile being obtained by exciting the sample with light at a wavelength of about 351 nm and then measuring the native fluorescence emitted therefrom at a wavelength about 450 nm.
Figure 16:
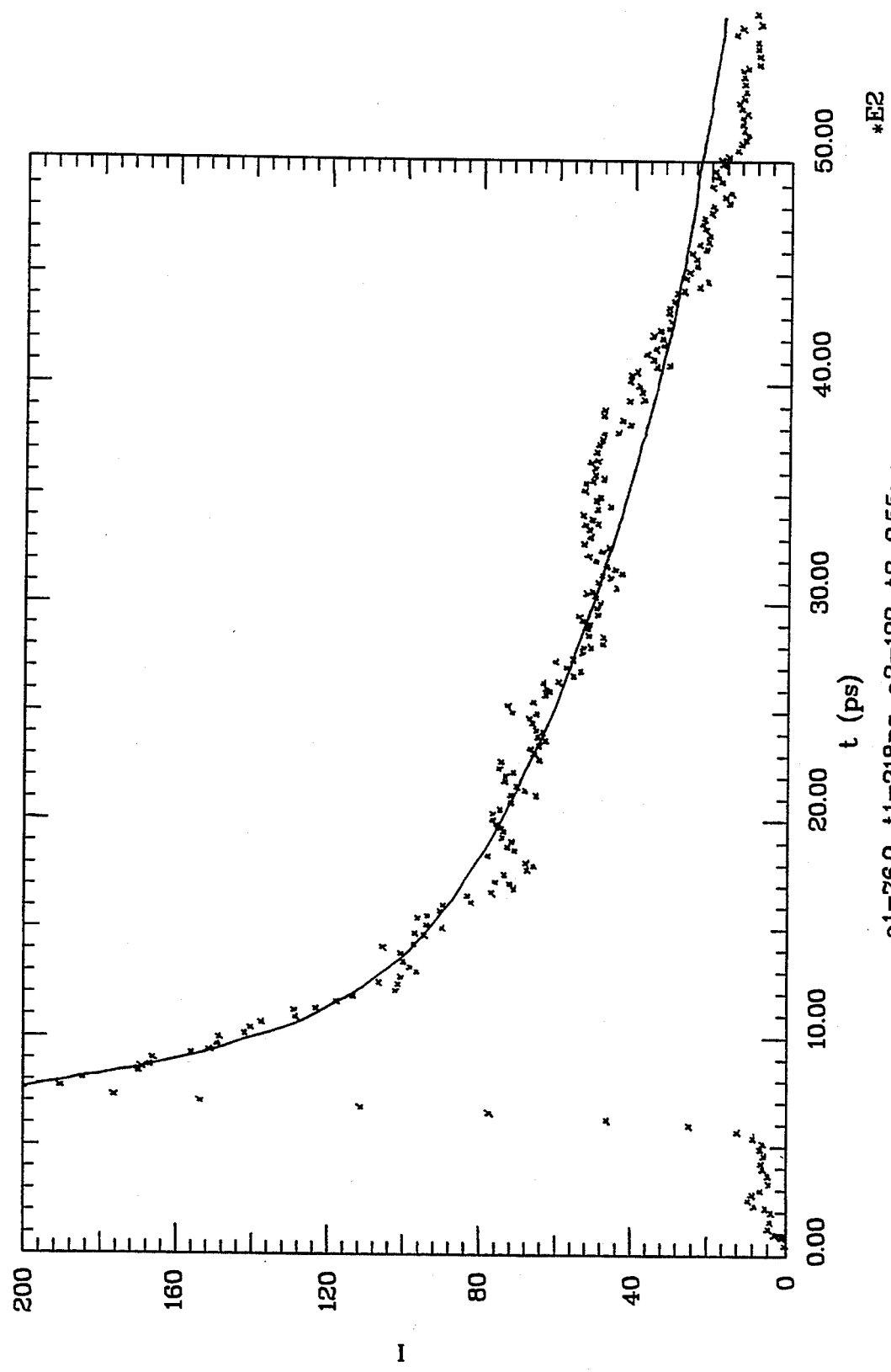
FIG. 16 is a time-resolved fluorescence profile of a normal human ovarian tissue sample, the profile being obtained by exciting the sample with light at a wavelength of about 351 nm and then measuring the native fluorescence emitted therefrom at a wavelength of about 450 nm.

The above-described technique was also applied to the detection of cancer in ovarian tissue as seen in FIGS. 15 and 16, which illustrate the time-resolved fluorescence profiles of a malignant human ovarian tissue sample and a normal human ovarian tissue sample, respectively, the profiles being obtained by exciting the sample with light at a wavelength of about 351 nm and then measuring the native fluorescence emitted therefrom at a wavelength of about 450 nm. When the profiles were fitted to the double exponential equation described above, it was observed that the fast component ($\tau_1$) of the malignant tissue was appreciably faster (178 ps rs. 218) than that of the normal tissue whereas the slow component ($\tau_2$) of the malignant tissue was appreciably slower (2.77 ns rs. 2.55 ns) than that of the normal tissue.

Finally, the above-described technique may also be applied to differentiating other abnormal or diseased states, besides cancer, from normal states In various types of tissues.

It is to be understood that various different types of optical instruments may be used to deliver the excitation light to the tissue sample and/or to collect the fluorescent light emitted therefrom for in vivo and/or in vitro applications. Such instruments may include lenses, endoscopes, optical fibers with hypodermic needles, microscopes, and the like.

The embodiments of the present invention are intended to be merely exemplary and those skilled In the art shall be able to make numerous variations and modifications to it without departing from the spirit of the present invention. All such variations and modifications are intended to be within the scope of the present invention as defined in the appended claims.

What is claimed is:

1. A method for determining if a human breast tissue sample is malignant as opposed to non-malignant comprising:
   a) irradiating the human breast tissue sample with a pulse of light at a wavelength of about 310 nm;
   b) measuring a native time-resolved fluorescence emitted therefrom at a wavelength of about 340 nm; and
   c) determining the condition of the human breast tissue sample in accordance with said measurement.

2. The method as claimed in claim 1 wherein said determining step comprises comparing the native time-resolved fluorescence emitted from the human breast tissue sample to that emitted from known malignment and non-malignment human breast tissues.

3. A method for determining if a human breast tissue sample is malignment as opposed to non-malignment comprising:
   a) irradiating the human breast tissue sample with a pulse of light at a wavelength of about 310 nm;
   b) measuring a native time-resolved fluorescence emitted therefrom at a wavelength of about 340 nm; and
   c) determining the condition of the human breast tissue sample in accordance with said measurement wherein said determining step comprises fitting a profile of the native time-resolved fluorecence emitted from the human breast tissue sample to a double exponential of the formula $$I(t) = A_1 e^{(\frac{-t}{\tau 1})} + A_2 e^{(\frac{-t}{\tau 2})}$$

and determining if $\tau_2$ is less than 1.6 ns whereby the human breast tissue sample is non-malignant or greater than 1.6 ns whereby the human breast tissue sample is malignant.

4. A method for determining if a human breast tissue sample is malignant as opposed to non-malignant comprising:
   a) irradiating the human breast tissue sample with a pulse of light at a wavelength of about 310 nm;
   b) measuring a native time-resolved fluorescence emitted therefrom at a wavelength of about 340 nm; and
   c) determining the condition of the human breast tissue sample in accordance with said measurement wherein said determining step comprising fitting a profile of the native time-resolved fluorescence emitted from the human breast tissue sample to a double exponential of the formula $$I(t) = A_1 e^{(\frac{-t}{\tau 1})} + A_2 e^{(\frac{-t}{\tau 2})}$$

and determining if $A_1/A_2$ is greater than 0.85 whereby the human breast tissue sample is non-malignant or less than 0.6 whereby the human breast tissue sample is malignant.

5. A method for determining if a tissue sample selected from the group consisting of human breast tissue and human ovarian tissue is malignant as opposed to non-malignant comprising:
   a) irradiating the tissue sample with light at a wavelength of about 353 nm;
   b) measuring a native time-resolved fluorescence emitted therefrom over one or more wavelength in a spectral band from about 400 nm to about 500 nm; and
   c) determining the condition of the tissue sample in accordance with said measurement.

6. The method as claimed in claim 5 wherein said determining step comprises comparing the native time-resolved fluorescence emitted from the tissue sample to that emitted from known malignant and non-malignant tissues of the same type of tissue.

7. The method as claimed in claim 5 wherein the tissue sample is human breast tissue and wherein the native time-resolved fluorescence is measured at about 400 nm.

8. The method as claimed in claim 5 wherein the native time-resolved fluorescence is measured at about 450 nm.

9. The method as claimed in claim 5 wherein the tissue sample is human breast tissue and wherein the native time-resolved fluorescence is measured at about 500 nm.

10. The method as claimed in claim 5 wherein the tissue sample is human breast tumor tissue.

11. A method for determining if a human breast tissue sample is malignant as opposed to non-malignant comprising:
   a) irradiating the human breast tissue sample with a pulse of light at a wavelength of about 353 nm;
   b) measuring a native-time resolved fluorescence emitted therefrom over one or more wavelengths in a spectral band from about 400 nm to about 500 nm; and
   c) determining the condition of the human breast tissue sample in accordance with said measurement wherein said determining step comprises fitting a profile of the native time-resolved fluorescence emitted from the human breast tissue sample to a double exponential of the formula $$I(t) = A_1 e^{(\frac{-t}{\tau 1})} + A_2 e^{(\frac{-t}{\tau 2})}$$

and determining if $\tau_1$ is less than about 150 ps whereby the human breast tissue sample is malignant or greater than about 200 ps whereby the human breast tissue sample is non-malignant.

12. A method for determining if a human breast tissue sample is malignant as opposed to non-malignant comprising:
   a) irradiating the human breast tissue sample with a pulse of light at a wavelength of about 353 nm;
   b) measuring a native time-resolved fluorescent emitted therefrom over one or more wavelengths in a spectral band from about 400 nm to about 500 nm; and
   c) determining the condition of the human breast tissue sample in accordance with said measurement wherein said determining step comprises fitting a profile of the native tissue-resolved fluorescence emitted from the human breast tissue sample to a double exponential of the formula $$I(t) = A_1 e^{(\frac{-t}{\tau 1})} + A_2 e^{(\frac{-t}{\tau 2})}$$

and determining if $\tau_2$ is greater than 2.4 ns whereby the human breast tissue sample is malignant or less than 2.4 ns whereby the human tissue sample is non-malignant.

13. A method for determining if a tissue sample selected from the group consisting of human breast tissue and human lung tissue is malignant as opposed to normal, said method comprising:
   a) irradiating the tissue sample with light at a wavelength of about 530 nm;
   b) measuring a native time-resolved fluorescence emitted therefrom over tone or more wavlengths in a spectral band from about 500 nm to about 600 nm; and
   c) determining the condition of the tissue sample in accordance with said measurement.

14. The method as claimed in claim 13 wherein said determining step comprises comparing the native time-resolved fluorescence emitted from the tissue sample to that emitted from known malignment and normal tissues of the same type of tissue.

15. The method as claimed in claim 13 wherein the native time-resolved fluorescence is measured at about 600 nm.

16. A method for determine if a tissue sample selected from the group consisting of malignant tissue and normal tissue is malignant comprising:
   a) irradiating the tissue sample with a pulse of light at a wavelength of about 530 nm;
   b) measuring a native time-resolved fluorescence emitted therefrom over one or more wavlengths in a spectral band from about 550 nm to about 600 nm; and
   c) determining the condition of the tissue sample in accordance with said measurement wherein said determining step comprises fitting a profile of the native time-resolved fluorescence emitted from the tissue sample to a double exponential of the formula $$I(t) = A_1 e^{(\frac{-t}{\tau 1})} + A_2 e^{(\frac{-t}{\tau 2})}$$

and determining if $\tau_1$ is about 100 ps whereby the tissue sample is malignant or about 200 ps whereby the tissue sample is normal.

* * * * *